United States Patent
Litvak et al.

(10) Patent No.: US 10,595,134 B1
(45) Date of Patent: *Mar. 17, 2020

(54) SYSTEMS AND METHODS FOR DETECTING AND REACTING TO SYSTEM NOISE GENERATED BY A COCHLEAR IMPLANT SYSTEM

(71) Applicant: Advanced Bionics AG, Staefa (CH)

(72) Inventors: Leonid M. Litvak, Los Angeles, CA (US); Eugene Kim, Thousand Oaks, CA (US); John Norris, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/455,523

(22) Filed: Jun. 27, 2019

Related U.S. Application Data

(63) Continuation-in-part of application No. 15/469,402, filed on Mar. 24, 2017, now Pat. No. 10,368,173.

(51) Int. Cl.
*H04R 25/00* (2006.01)
*A61N 1/02* (2006.01)
(Continued)

(52) U.S. Cl.
CPC ........... *H04R 25/353* (2013.01); *A61N 1/025* (2013.01); *A61N 1/36038* (2017.08);
(Continued)

(58) Field of Classification Search
CPC .. H04R 25/505; H04R 25/353; H04R 25/356; H04R 25/606; H04R 25/50; H04R 25/70;
(Continued)

(56) References Cited

U.S. PATENT DOCUMENTS

| 4,185,168 A | 1/1980 | Graupe et al. |
| 7,515,966 B1 | 4/2009 | Litvak et al. |

(Continued)

FOREIGN PATENT DOCUMENTS

| EP | 2375787 | 9/2013 |
| EP | 2352148 | 10/2013 |
| WO | 2015170140 | 11/2015 |

OTHER PUBLICATIONS

Non-Final Office Action received in U.S. Appl. No. 15/469,402 dated Dec. 13, 2018.
(Continued)

*Primary Examiner* — Joshua Kaufman
(74) *Attorney, Agent, or Firm* — ALG Intellectual Property, LLC

(57) ABSTRACT

An exemplary sound processor included in a cochlear implant system used by a recipient is configured to generate a spectral input signal representative of spectral energy contained within a frequency band of a plurality of frequency bands of an audio input signal presented to the recipient. The sound processor further receives a predetermined system noise threshold that is determined prior to the audio input signal being presented to the recipient and that is based on a predicted or measured spectral energy level of system noise generated by a theoretical or test cochlear implant system associated with, but distinct from, the cochlear implant system. The sound processor determines whether a spectral energy level of the spectral input signal exceeds the system noise threshold and, based on this determination, performs an action that impacts stimulation provided to the recipient by the cochlear implant system. Corresponding methods and systems are also disclosed.

26 Claims, 11 Drawing Sheets

(51) Int. Cl.
  *A61N 1/36*  (2006.01)
  *A61N 1/05*  (2006.01)
(52) U.S. Cl.
  CPC ........... *H04R 25/30* (2013.01); *H04R 25/505* (2013.01); *A61N 1/0541* (2013.01); *H04R 2225/43* (2013.01); *H04R 2225/67* (2013.01)
(58) Field of Classification Search
  CPC .... H04R 2225/67; H04R 25/41; H04R 25/43; G10L 21/0208; G10L 21/0216
  See application file for complete search history.

(56) References Cited

U.S. PATENT DOCUMENTS

| | | |
|---|---|---|
| 7,953,490 B1 | 5/2011 | Fridman |
| 8,706,245 B2 | 4/2014 | Case et al. |
| 9,036,830 B2 | 5/2015 | Tanaka et al. |
| 10,368,173 B1 * | 7/2019 | Litvak ................. H04R 25/353 |
| 2016/0064947 A1 | 3/2016 | Heresztyn et al. |
| 2017/0347213 A1 | 11/2017 | Goorevich et al. |

OTHER PUBLICATIONS

Boll, et al., Suppression of Acoustic Noise in Speech using Spectral Subtraction, IEEE Transaction on Acoustics, Speech and Signal Processing, ASSP-27, pp. 113-120 (1979).
McNally, et al., Dynamic Range Control of Digital Audio Signals, J. Audio. Eng. Soc. vol. 32, No. 5 pp. 316-327, 1984.

* cited by examiner

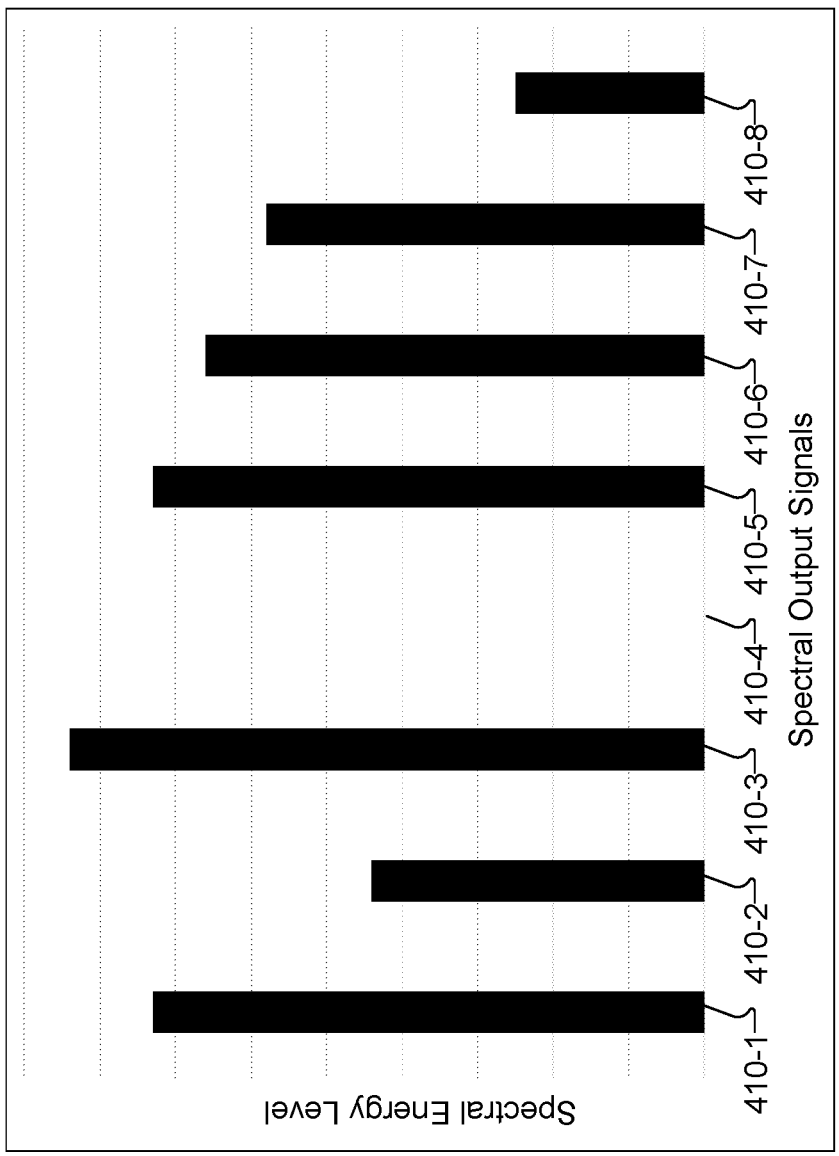

SYSTEMS AND METHODS FOR DETECTING AND REACTING TO SYSTEM NOISE GENERATED BY A COCHLEAR IMPLANT SYSTEM

RELATED APPLICATIONS

The present application is a continuation-in-part application of U.S. patent application Ser. No. 15/469,402, filed Mar. 24, 2017, and entitled "Systems and Methods for Minimizing an Effect of System Noise Generated by a Cochlear Implant System," which application is incorporated herein by reference in its entirety.

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Some types of conductive hearing loss occur when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from severe to profound sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of an array of electrodes implanted within the cochlea. Direct stimulation of the auditory nerve fibers leads to the perception of sound in the brain and at least partial restoration of hearing function.

Unfortunately, in some circumstances, noise (e.g., electrical noise, radio frequency ("RF") noise, etc.) may be inadvertently introduced into electrical signals that include encoded acoustic information. Such noise may interfere with or mask useful information encoded into the electrical signals, particularly in quiet environments where the magnitude of the useful information encoded into the electrical signals is relatively small. One potential source of such noise may be the cochlear implant system itself.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

FIG. 9 illustrates a plurality of exemplary spectral output signals that may be generated by the sound processor of FIG. 3 to minimize an effect of system noise generated by a cochlear implant system according to principles described herein.

DETAILED DESCRIPTION

Figure 1:
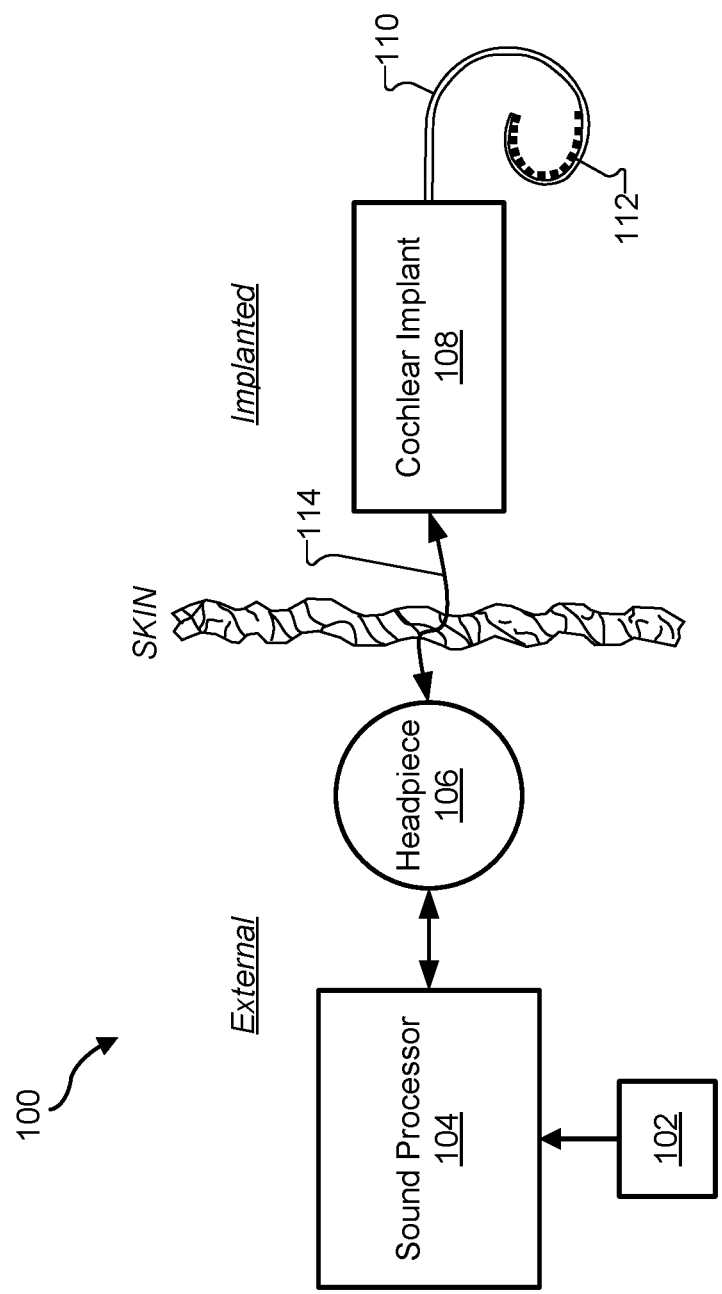
FIG. 1 illustrates an exemplary cochlear implant system according to principles described herein.

Systems and methods for detecting and reacting to system noise generated by a cochlear implant system used by a recipient (e.g., a cochlear implant system patient) are described herein. For example, the cochlear implant system may include a sound processor configured to process audio input signals presented to the recipient and a cochlear implant configured to be implanted within the recipient to apply electrical stimulation representative of the audio input signals to the recipient. In certain examples, the sound processor may process an audio input signal (e.g., a time-domain audio input signal) that is presented to the recipient and may generate, based on the processing, a spectral input signal representative of spectral energy contained within a frequency band included in a plurality of frequency bands of the audio input signal. The sound processor may also receive a predetermined system noise threshold that is determined prior to the audio input signal being presented to the recipient. For example, the predetermined system noise threshold may be determined as part of the design and/or manufacturing of the sound processor and may be based on a predicted or measured spectral energy level of system noise generated by a theoretical or test cochlear implant system associated with, but distinct from, the cochlear implant system. For instance, the predetermined system noise threshold may be based on a computer model of system noise for the sound processor design or based on measurements of a test prototype of the sound processor. The sound processor may determine whether a spectral energy level (e.g., a power level) of the spectral input signal exceeds the predetermined system noise threshold.

Based on the determination of whether the spectral energy level of the spectral input signal exceeds the predetermined system noise threshold, the sound processor may react to system noise detected in the spectral input signal (e.g., based on the spectral energy level being determined to not exceed the predetermined system noise threshold) by performing an action that impacts stimulation provided to the recipient by the cochlear implant system. As will be described in more detail below, this action performed by the sound processor may be any suitable action to impact the stimulation.

As one exemplary action to impact the stimulation, for instance, the sound processor may generate a spectral output signal based on the determination of whether the spectral energy level of the spectral input signal exceeds the predetermines system noise threshold. For example, the sound processor may include the spectral input signal in the spectral output signal if the spectral energy level exceeds the predetermined system noise threshold and may exclude the spectral input signal from the spectral output signal if the spectral energy level does not exceed the predetermined system noise threshold. The sound processor may then direct the cochlear implant to apply electrical stimulation representative of the spectral output signal to the recipient.

As another exemplary action to impact the stimulation, the sound processor may alter how different audio input sources are mixed or weighted in the stimulation. Specifically, in these examples, the sound processor may receive a plurality of audio input signals (one of which is the audio input signal mentioned above) from a plurality of audio input devices included in the cochlear implant system, and may assign a dynamic weighting factor to each audio input signal of the plurality of audio input signals. The dynamic weighing factors may be configured, for example, to define how the plurality of audio input signals is mixed in the stimulation provided to the recipient, and, accordingly, the audio input signal mentioned above may be assigned a particular dynamic weighting factor and may be provided by a particular audio input device of the plurality of audio input devices. In these cases, then, the performing of the action that impacts the stimulation provided to the recipient may include 1) detecting, based on the determination of whether the spectral energy level of the spectral input signal exceeds the predetermined system noise threshold, a toggling off or on of the particular audio input device; and 2) revising, based on the detection of the toggling, the particular dynamic weighting factor assigned to the audio input signal. In this way, as will be described in more detail below, when sufficient system noise is detected so as to show (or make it likely) that a particular source of audio input has been turned on or off, the sound processor may automatically begin or cease mixing audio from the source into the stimulation presented to the recipient, as may be merited by the situation.

As used herein, "system noise" refers to any noise in a cochlear implant system that is introduced by the cochlear implant system itself (i.e., any of the components included the cochlear implant system). In some examples, the system noise may interfere with and/or prevent a recipient from perceiving and/or understanding content included in an audio input signal that is presented to the recipient. System noise may include, but is not limited to, electrical noise, RF noise, thermal noise (e.g., Johnson-Nyquist noise), coupled noise, and/or any other disturbance or noise introduced by the cochlear implant system itself or any component thereof (e.g., a audio input device, a sound processor, a wireless communication component such as a headpiece, etc.). System noise may be inherently included in each of the spectral input signals generated by the sound processor.

As used herein, a "system noise threshold" is associated with a spectral energy level of system noise introduced by a cochlear implant system in a particular portion of an audio spectrum. The system noise threshold may be based on an actual spectral energy level of the system noise as measured by the sound processor and/or a measuring device separate from the cochlear implant system, an estimated or predicted spectral energy level of the system noise, and/or any other suitable representation of the system noise as may serve a particular implementation. In some examples, the system noise threshold is set to be slightly higher than the actual, estimated, or predicted system noise level.

As will be described in more detail below, if a spectral input signal has a spectral energy level that does not exceed the system noise threshold, the spectral input signal may be considered to contain principally or solely system noise. Even if the spectral input signal were to contain useful information (e.g., content of interest such as speech or music content), if its spectral energy level does not exceed the system noise threshold, the system noise will mask the content of interest and thereby prevent the recipient from perceiving the content of interest if electrical stimulation representative of the spectral input signal were applied to the recipient. In contrast, if a spectral input signal has a spectral energy level that exceeds the system noise threshold, the useful information or content of interest included in the spectral input signal may not be entirely masked by system noise that may be present in the spectral input signal.

System noise included in one portion of an audio spectrum may affect a recipient's perception of sounds in surrounding portions of the audio spectrum. For example, system noise included in a particular frequency band may make it difficult for the recipient to perceive content of interest in adjacent frequency bands, even if the spectral input signals associated with the adjacent frequency bands have spectral energy levels that are greater than the system noise thresholds for the adjacent frequency bands. This is especially the case in scenarios in which a cochlear implant recipient is trying to perceive relatively quiet sounds in a relatively quiet environment.

It will be understood that in the context of audio input signals generally (e.g., audio input signals that are to be presented acoustically by way of a loudspeaker or the like), it may be impractical or impossible to reduce system noise by excluding noise energy associated with particular frequency bands (e.g., by excluding a spectral input signal from a spectral output signal as described herein). Instead, to reduce noise associated with particular frequency bands, an audio input signal would typically need to be divided (e.g., by way of an algorithm to generate a plurality of spectral input signals associated with respective frequency bands), analyzed (e.g., to reduce the noise associated with particular frequency bands), and then resynthesized before being presented to a user. Without the final resynthesis step, the acoustic signal presented to the user based on the original audio input signal may sound incorrect (e.g., may appear to have an incorrect tone, a synthetic timbre, etc.) or may even be unrecognizable as the original audio input signal. In contrast, however, the situation is different in the context of cochlear implants, where the stimulation is directly and electrically (i.e., rather than acoustically) delivered to specific nerve fibers of a recipient that are adapted for each respective frequency band represented. In this case, a resynthesis of the audio input signal after analyzing the plurality of spectral input signals to reduce system noise may be unnecessary and inefficient. Instead, most or all of the energy associated with a spectral input signal that is determined to predominantly carry system noise can be excluded so as to not be represented in the electrical stimulation that is applied to the recipient.

Hence, by excluding a spectral input signal from a spectral output signal when a spectral energy level of the spectral input signal is lower than a predetermined system noise threshold that corresponds to the same frequency band as the spectral input signal, the sound processor may avoid directing the cochlear implant to apply electrical stimulation representative of spectral noise included in the spectral input signal to the recipient. This may improve a recipient's perception of sounds (e.g., relatively quiet sounds) in some circumstances such as in quiet environments where system noise may be the most significant signal source in various portions of the frequency spectrum. Additional or alternative benefits will be made apparent by the following description.

Various embodiments will now be described in more detail with reference to the figures. The disclosed systems and methods may provide one or more of the benefits mentioned above and/or various additional and/or alternative benefits that will be made apparent herein.

FIG. 1 shows an exemplary cochlear implant system 100. As shown, cochlear implant system 100 may include various components configured to be located external to a cochlear implant recipient including, but not limited to, an audio input device 102, a sound processor 104, and a headpiece 106. Cochlear implant system 100 may further include various components configured to be implanted within the recipient including, but not limited to, a cochlear implant 108 (also referred to as an implantable cochlear stimulator) and a lead 110 (also referred to as an intracochlear electrode array) with a plurality of electrodes 112 disposed thereon. In certain examples, additional or alternative components may be included within cochlear implant system 100 as may serve a particular implementation. It will be understood that in certain implementations (e.g., "fully implantable" implementations), one or more of the components described and illustrated as being external to the recipient may alternatively be implanted within the recipient. The components shown in FIG. 1 will now be described in more detail.

Audio input device 102 may be configured to detect audio input signals presented to the recipient. Audio input device 102 may be implemented in any suitable manner. For example, audio input device 102 may include a microphone such as a T-MIC™ microphone from Advanced Bionics. Such a microphone may be associated with a particular ear of the recipient such as by being located in a vicinity of the particular ear (e.g., within the concha of the ear near the entrance to the ear canal) or held within the concha of the ear near the entrance of the ear canal by a boom or stalk that is attached to an ear hook configured to be selectively attached to sound processor 104. In other examples, audio input device 102 may be implemented by one or more microphones disposed within headpiece 106, one or more microphones disposed within sound processor 104, one or more beam-forming microphones, and/or any other suitable microphone or microphones as may serve a particular implementation. Additionally or alternatively, audio input device 102 may be implemented as an audio source other than the microphones described above. For instance, audio input device 102 may be implemented as a telecoil, as a digital device (e.g., a Bluetooth device, an FM device, a mobile device, a media player device, etc.) that provides prerecorded audio or audio received from an audio source such as a digital media service, as a remote microphone that captures and transmits an audio input signal, and/or as any other suitable source of an audio input signal that may be presented to the recipient in a particular implementation.

Sound processor 104 (e.g., at least one physical computing component included in sound processor 104) may be configured to direct cochlear implant 108 to generate and apply electrical stimulation (also referred to herein as "stimulation current") representative of one or more audio input signals (e.g., one or more audio input signals detected by audio input device 102) to one or more stimulation sites associated with an auditory pathway (e.g., the auditory nerve) of the recipient. Exemplary stimulation sites include, but are not limited to, one or more locations within the cochlea, the cochlear nucleus, the inferior colliculus, and/or any other nuclei in the auditory pathway. While, for the sake of simplicity, electrical stimulation will be described herein as being applied to one or both cochleae of a recipient, it will be understood that stimulation current may also be applied to other suitable nuclei in the auditory pathway. To this end, sound processor 104 may process the one or more audio input signals in accordance with a selected sound processing strategy or program (i.e., a selected sound processing program) to generate appropriate stimulation parameters for controlling cochlear implant 108.

Sound processor 104 may include or be implemented by a behind-the-ear ("BTE") unit, a body worn device, and/or any other sound processing unit as may serve a particular implementation. Additionally, as will be described in more detail below, sound processor 104 may include at least one physical computing component (e.g., a processor, a memory, a storage device, etc.) implementing one or more system noise management systems for detecting and reacting to system noise generated by cochlear implant system 100, as will be described in more detail below.

In certain implementations, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bidirectional communication link and/or one or more dedicated unidirectional communication links. In some examples, sound processor 104 may execute and operate in accordance with a sound processing program that has been loaded into memory contained within sound processor 104.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the recipient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via communication link 114.

Cochlear implant 108 may include any type of implantable stimulator that may be used in association with the apparatuses and methods described herein. For example, cochlear implant 108 may be implemented by an implantable cochlear stimulator. In some alternative implementations, cochlear implant 108 may include a brainstem implant and/or any other type of active implant or auditory prosthesis that may be implanted within a recipient and configured to apply stimulation to one or more stimulation sites located along an auditory pathway of a recipient.

In some examples, cochlear implant 108 may be configured to generate and apply electrical stimulation (e.g., representative of an audio input signal provided by audio input device 102 and processed by sound processor 104) in accordance with one or more stimulation parameters transmitted thereto by sound processor 104. Cochlear implant 108 may be further configured to apply the electrical stimulation to one or more stimulation sites within the recipient via one or more electrodes 112 disposed along lead 110 (e.g., by way of one or more electrodes 112). In some examples, cochlear implant 108 may include a plurality of independent current sources each associated with a stimulation channel defined by one or more of electrodes 112. In this manner, different stimulation current levels may be applied to multiple stimulation sites simultaneously (also referred to as "concurrently") by way of multiple electrodes 112.

Stimulation current may be represented by one or more stimulation waveforms. A stimulation waveform may visually indicate stimulation current (e.g., energy levels of stimulation current, duration of application of stimulation current, etc.) that sound processor 104 may direct cochlear implant 108 to apply to the recipient by way of one or more electrodes 112.

Figure 2:
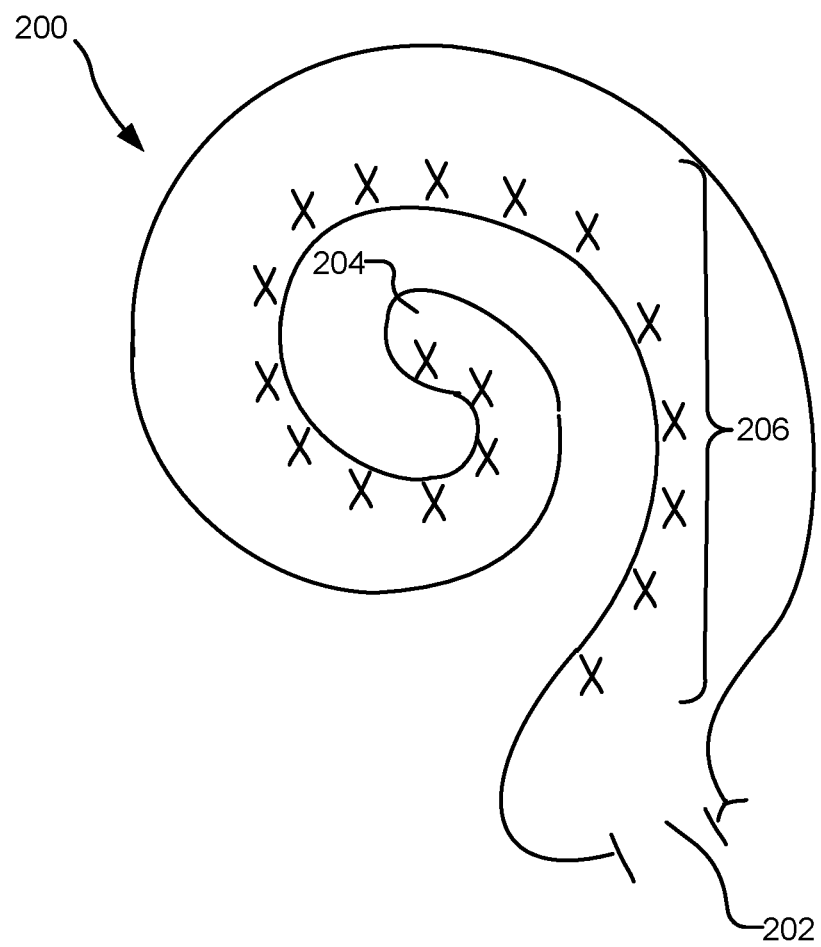
FIG. 2 illustrates a schematic structure of the human cochlea according to principles described herein.

FIG. 2 illustrates a schematic structure of a human cochlea 200 into which lead 110 may be inserted. As shown in FIG. 2, cochlea 200 is in the shape of a spiral beginning at a base 202 and ending at an apex 204. Within cochlea 200 resides auditory nerve tissue 206, which is denoted by Xs in FIG. 2. Auditory nerve tissue 206 is organized within cochlea 200 in a tonotopic manner. That is, relatively low frequencies are encoded at or near apex 204 of cochlea 200 (referred to as an "apical region") while relatively high frequencies are encoded at or near base 202 (referred to as a "basal region"). Hence, each location along the length of cochlea 200 corresponds to a different perceived frequency. Cochlear implant system 100 may therefore be configured to apply electrical stimulation to different locations within cochlea 200 (e.g., different locations along auditory nerve tissue 206) to provide a sensation of hearing to the recipient. For example, when lead 110 is properly inserted into cochlea 200, each of electrodes 112 may be located at a different cochlear depth within cochlea 200 (e.g., at a different part of auditory nerve tissue 206) such that stimulation current applied to one electrode 112 may cause the recipient to perceive a different frequency than the same stimulation current applied to a different electrode 112 (e.g., an electrode 112 located at a different part of auditory nerve tissue 206 within cochlea 200).

Figure 3:
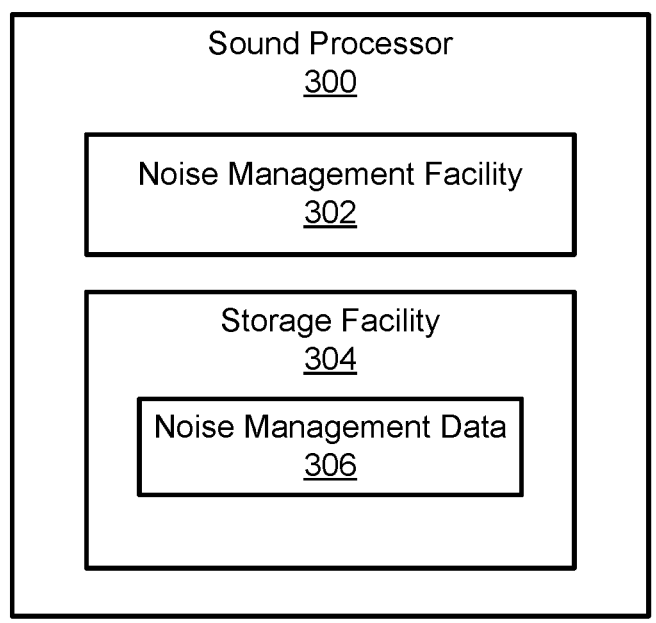
FIG. 3 illustrates exemplary components of a sound processor that detects and reacts to system noise generated by a cochlear implant system according to principles described herein.

FIG. 3 illustrates exemplary components of a sound processor 300 configured to detect and react to system noise generated by a cochlear implant system. As will be described below, sound processor 300 may detect and react to the system noise in different ways, including by preventing at least some of the system noise from being included in a spectral output signal used to generate stimulation applied to the recipient, by remixing different audio input signals received by sound processor 300 in different ways, and/or in other suitable manners.

Sound processor 300 may be the same as or similar to sound processor 104 (e.g., an exemplary implementation of sound processor 104) shown in FIG. 1. As such, sound processor 300 may be described in certain examples herein to be included within a cochlear implant system such as cochlear implant system 100. As shown, sound processor 300 may include, without limitation, a noise management facility 302 and a storage facility 304 selectively and communicatively coupled to one another. It will be recognized that although facilities 302 and 304 are shown to be separate facilities in FIG. 3, facilities 302 and 304 may be combined into fewer facilities, such as into a single facility, or divided into more facilities as may serve a particular implementation. Facilities 302 and 304 may each be implemented by one or more physical computing components or devices (e.g., processors, memory units, communication interfaces, etc.) included in sound processor 300. Facilities 302 and 304 will now be described in more detail.

Noise management facility 302 may perform various operations associated with detecting and reacting to system noise generated by a cochlear implant system. For example, noise management facility 302 may generate a spectral input signal representative of spectral energy contained within a frequency band in a plurality of frequency bands of an audio input signal presented to a cochlear implant recipient.

As used herein, a "spectral signal" (e.g., a spectral input signal, a spectral output signal, etc.) includes any frequency-domain signal representative of energy within a distinct band of an audio spectrum during a particular period of time. As such, a "spectral energy level" of a spectral signal may refer to an amount of energy included in the distinct band of the audio spectrum represented by the spectral signal. Thus, for example, the spectral input signal generated by noise management facility 302 may refer to a frequency-domain signal associated with a band of an audio spectrum (e.g., 5.0 kHz to 5.2 kHz), and may include energy having different spectral energy levels at different times (e.g., a spectral energy level of 10 dB at one particular time followed by a spectral energy level of 5 dB at a later time, and the like).

Noise management facility 302 may generate the spectral input signal in any way as may serve a particular implementation. For example, noise management facility 302 may generate the spectral input signal by receiving an audio input signal presented to the recipient (e.g., by way of an audio input device such as audio input device 102) and dividing the audio input signal into a plurality of spectral input signals each corresponding to different respective frequency bands (i.e., including the spectral input signal representative of the spectral energy contained within the frequency band).

Noise management facility 302 may divide the audio input signal in any suitable way. For example, noise management facility 302 may process the audio input signal in accordance with a Fast Fourier Transform ("FFT") algorithm, which may result in a plurality of spectral signals that each correspond to particular frequency bins (i.e., frequency bands or portions of the audio spectrum) that may be referred to herein as an FFT bins. For example, an FFT algorithm may divide an audio input signal into a number of FFT bins (e.g., 128 FFT bins) that are each representative of a portion of an audio spectrum (e.g., 1 kHz to 2 kHz, 5.0 kHz to 5.2 kHz, 15 kHz to 20 kHz, etc.). In other words, the FFT algorithm may associate, with each portion of the audio spectrum (i.e., with each FFT bin), a signal representative of a spectral energy level or power level that corresponds to the respective portion of the audio spectrum.

The spectral input signal generated by noise management facility 302 may correspond to (i.e., correlate with, be associated with, etc.) any channel or frequency band as may serve a particular implementation. For instance, in certain examples, the spectral input signal may correspond to a particular frequency bin included in the plurality of frequency bins associated with the FFT algorithm (i.e., a particular FFT bin). In other examples, the spectral input signal may correspond to a set of frequency bins (e.g., a frequency-contiguous set of FFT bins) selected from the plurality of frequency bins associated with the FFT algorithm. For instance, noise management facility 302 may select a frequency-contiguous set of FFT bins and generate the spectral input signal to represent a spectral energy level that corresponds to an average spectral energy of the frequency-contiguous set of frequency bins. In yet other examples, the spectral input signal may correspond to a channel (e.g., an analysis channel, a stimulation channel, etc.) associated with sound processor 300. Various benefits associated with correlating the spectral input signal with different types or sizes of frequency bands will be described below.

Along with generating the spectral input signal, noise management facility 302 may receive a predetermined system noise threshold. For example, the predetermined system noise threshold may be determined prior to the audio input signal being presented to the recipient and may be based on a predicted or measured spectral energy level of system noise generated by a theoretical or test cochlear implant system associated with, but distinct from, the cochlear implant system. In some examples, the predetermined system noise threshold may be based on a characterization of system noise generated by the cochlear implant system within the frequency band associated with the spectral input level. The predetermined system noise threshold may be predetermined in the sense that the predetermined system noise threshold is determined prior to use by noise management facility 302 for comparing with the spectral energy level of the spectral input signal to determine whether the spectral energy level exceeds the predetermined system noise threshold. This predetermination of the predetermined system noise threshold may be performed by noise management facility 302 or another facility or component of sound processor 300, by cochlear implant system 100, or by another system associated with cochlear implant system 100 (e.g., a manufacturing test system), and may be performed in any manner as may serve a particular implementation.

For example, as will be described in more detail below, noise management facility 302 may receive a test frequency domain signal that is representative of system noise within a frequency band associated with a spectral input signal. Noise management facility 302 may then determine an amplitude of the test frequency domain signal, and may set the predetermined system noise threshold to a value associated with the determined amplitude of the test frequency domain signal (e.g., within a predetermined amount of the determined amplitude).

In other examples, the predetermined system noise threshold may be predetermined based on other types of measurements (e.g., based on an actual spectral energy level of the system noise as measured by noise management facility 302, by another component of sound processor 300 or cochlear implant system 100, and/or by a measuring device separate from the cochlear implant system such as a manufacturing test system or the like) or based on a spectral energy level of the system noise that is predicted, theoretically calculated, estimated, required by system specifications, or the like. In some examples, the system noise threshold is set to be slightly higher than the actual, estimated, or predicted system noise level. Methods by way of which the received system noise threshold is generated will be further described in more detail below. Noise management facility 302 may determine (e.g., receive, access, etc.) the predetermined system noise threshold by accessing data representative of the predetermined system noise threshold from a lookup table stored in storage facility 304 or another suitable location.

Once the predetermined system noise threshold has been determined, noise management facility 302 may receive or otherwise access the predetermined system noise threshold, and may determine whether the spectral energy level of the spectral input signal exceeds the predetermined system noise threshold in any suitable manner.

Based on the determination of whether the spectral energy level of the spectral input signal exceeds the predetermined system noise threshold, noise management facility 302 may perform an action that impacts stimulation provided to the recipient by the cochlear implant system. For example, noise management facility 302 may perform an action of generating a spectral output signal (e.g., an output signal that may be used by sound processor 300 to direct a cochlear implant to apply stimulation to the recipient). Specifically, if noise management facility 302 determines that the spectral energy level of the spectral input signal is greater than the predetermined system noise threshold, noise management facility 302 may include the spectral input signal in the spectral output signal that is generated. Conversely, if noise management facility 302 determines that the spectral energy level of the spectral input signal does not exceed (e.g., is less than or equal to) the predetermined system noise threshold, noise management facility 302 may exclude the spectral input signal from the spectral output signal that is generated. Noise management facility 302 may generate a spectral output signal that excludes the spectral input signal in any suitable way. For example, noise management facility 302 may simply set a component of the spectral output signal that corresponds to the same portion of the audio spectrum associated with the spectral input signal to a spectral energy level of zero. In other examples, noise management facility 302 may include an alternative spectral signal (e.g., a spectral signal representative of "comfort noise" or the like) in the spectral output signal in place of the spectral input signal.

As another exemplary action that impacts stimulation, an implementation of sound processor 300 may be associated with a plurality of audio input devices that provide a plurality of audio input signals. As such, noise management facility 302 may perform an action of remixing or otherwise altering a manner in which stimulation representative of each different audio input signal is presented to the recipient. For example, noise management facility 302 may detect, based on the determination of whether the spectral energy level of the spectral input signal exceeds the predetermined system noise threshold, that a particular audio input device is toggled off or toggled on, and, in response, may revise a particular dynamic weighting factor assigned to the audio input signal as may be appropriate. Other suitable actions that impact stimulation may also be performed based on the detection of whether the spectral energy level of the spectral input signal exceeds the predetermined system noise threshold in some implementations. More detail about these actions that impact stimulation will be described in more detail below.

Storage facility 304 may maintain noise management data 306 and/or any other data received, generated, managed, maintained, used, and/or transmitted by noise management facility 302 in a particular implementation. Noise management data 306 may include data representative of one or more system noise thresholds, one or more noise profiles, one or more libraries of noise profiles, one or more system noise measurements, system noise characterizations, or the like. In addition to noise management data 306, storage facility 304 may further include any other data as may serve a particular implementation of sound processor 300 to facilitate performing one or more of the operations described herein.

Figure 4:
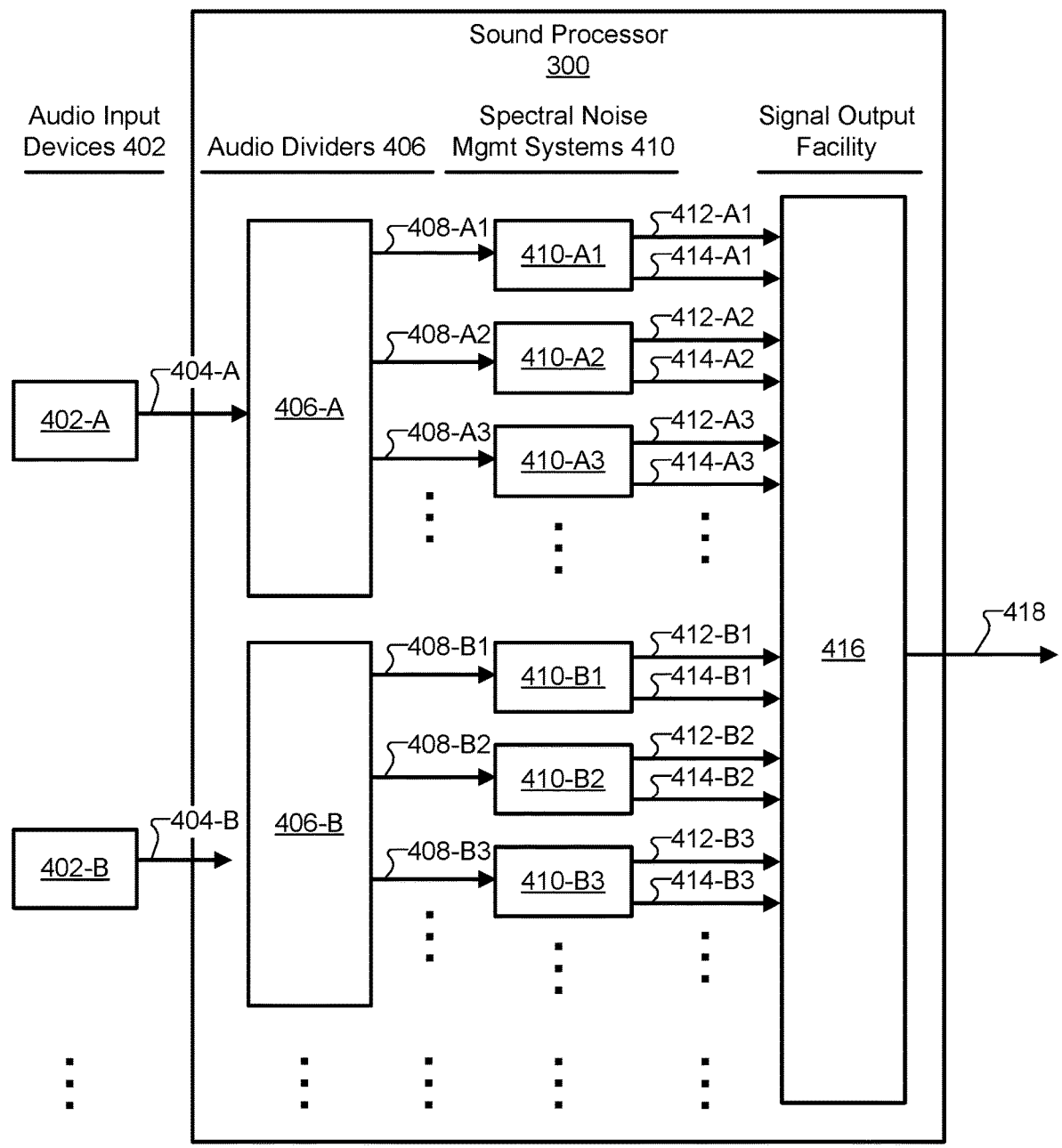
FIG. 4 illustrates an exemplary implementation of the sound processor of FIG. 3 according to principles described herein.

Sound processor 300 (including facilities 302 and 304 included therein) may perform the operations described above and/or any other operations described herein in any manner and/or using any hardware and/or software components or subsystems as may serve a particular implementation. For example, FIG. 4 shows an exemplary implementation of sound processor 300 that may be implemented in a cochlear implant system such as cochlear implant system 100 (e.g., to implement sound processor 104). The components shown in FIG. 4 may be configured to perform one or more of the operations described above with respect to facilities 302 and/or 304 of sound processor 300. It will be recognized that the components shown in FIG. 4 are merely representative of some of the various possible components that may be included in sound processor 300. For example, ellipsis throughout FIG. 4 will be understood to denote where additional like components may be included in sound processor 300 that are not explicitly shown. Additionally, sound processor 300 may include additional or alternative components (e.g., components unlike components explicitly shown in FIG. 4) as may serve a particular implementation.

As shown in FIG. 4, a plurality of audio input devices 402 (e.g., audio input devices 402-A and 402-B) may provide respective audio input signals 404 (e.g., audio input signals 404-A and 404-B) to sound processor 300. Audio input devices 402 may each be implemented as any of the types of audio input devices described herein, including any of the exemplary implementations of audio input device 102 described above in relation to FIG. 1. Audio input signals 404 may be processed by respective audio dividers 406 (e.g., an audio divider 406-A for audio input signal 404-A, an audio divider 406-B for audio input signal 404-B, etc.), which are configured to divide the respective audio input signals into respective pluralities of frequency domain signals. The frequency domain signals may each represent a distinct frequency portion (i.e., frequency band) of the audio input signal and are illustrated in FIG. 4 as spectral input signals 408 (e.g., spectral input signals 408-A1 through 408-A3 and 408-B1 through 408-B3).

A plurality of spectral noise management systems 410 (e.g., spectral noise management systems 410-A1 through 410-A3 and 410-B1 through 410-B3) may each receive a respective spectral input signal 408 (e.g., spectral noise management system 410-A1 receiving spectral input signal 408-A1, spectral noise management system 410-A2 receiving spectral input signal 408-A2, and so forth). Spectral noise management systems 410 may generate, based on respective spectral input signals 408, a plurality of spectral output signals 412 (e.g., spectral output signals 412-A1 through 412-A3, 412-B1 through 412-B3, etc.), as well as a plurality of noise indicator signals 414 (e.g., noise indicator signals 414-A1 through 414-A3, 414-B1 through 414-B3, etc.). These signals 412 and 414 are received and processed by a signal output facility 416 that may be configured to mix, map, multiplex, and otherwise process signals 412 and 414 to generate a transmission signal 418, which may be transmitted (e.g., by way of headpiece 106 and communication link 114) to cochlear implant 108 for use in applying electrical stimulation to the patient. Certain components of sound processor 300 shown in FIG. 4 will now be described in more detail with reference to FIGS. 5A through 10.

Audio input devices 402 may each be implemented as any of the audio input devices 402 described herein, such as a local microphone (e.g., a T-MIC, a BTE mic, etc.), a remote microphone transmitting a digitized audio signal, a mobile device or other sound device providing digital audio signals by way of Bluetooth, FM, or other wireless or wired technologies, a telecoil, or any other suitable audio input device. For example, audio input devices 402 may represent two of several microphones (e.g., a T-MIC microphone, a front microphone, a headpiece microphone, etc.) that may all be mixed and used together to provide stimulation to the cochlear implant system recipient. If audio input device 402-A is a T-MIC microphone, for example, and audio input device 402-B is a front microphone, sound processor 300 may generally give equal weight to the two microphones and utilize equally the respective audio input signals 404 that the microphones capture. To this end, sound processor 300 may assign a dynamic weighting factor to each audio input signal 404-A and 404-B (e.g., equal dynamic weighting factors in this example where the microphones are utilized equally).

Dynamic weighting factors may be configured to define how the plurality of audio input signals is mixed in the stimulation ultimately provided to the recipient. Thus, as will be described in more detail below, if it is determined that one of audio input device 402 is not providing significant input (e.g., because it has been toggled off), it may be desirable to dynamically change the weighting factor for that audio input device 402 to no longer utilize it to the same degree or at all. Conversely, if the weighting factors indicate that the signal from one of audio input devices 402 should be utilized exclusively because the other audio input device 402 is off, then it may be desirable to adjust the respective weighting factors when the audio input device 402 is detected to have been toggled back on so that both audio input devices 402 can be used again.

Different combinations of audio input devices 402 may call for different types of weighting factors. For instance, if a cochlear implant recipient is at a meeting listening to a speaker give a speech, audio input device 402-A may be a local microphone capturing sounds proximate to the recipient and audio input device 402-B may be a remote microphone worn by the speaker across the room and capturing the speech. In this example, it may be desirable for the remote microphone (i.e., audio input device 402-B) to be weighted in the mix presented to the recipient more heavily than the local microphone (i.e., audio input device 402-A), because the recipient may be more interested in hearing the speech than the environment noise surrounding him or her.

However, this may change if the speaker ends the talk (such that audio input device 402-B toggles off and only provides system and environmental noise) or if someone sitting next to the recipient leans over to whisper something (such that audio input device 402-A toggles on and begins providing something more than system and environmental noise). When these types of events happen, it may be desirable for the weighting or mixing of the different audio input devices to change dynamically. As will be described in more detail below, one action to impact simulation that sound processor 300 may perform based on determining whether a spectral energy level of a spectral input signal exceeds a predetermined system noise threshold is to dynamically adjust these weighting factors to ensure that the stimulation applied to the recipient represents the most relevant audio that the recipient is most likely to want to hear.

Audio dividers 406 may be implemented in hardware or software and may process respective audio input signals 404 to divide each audio input signal 404 into respective spectral input signals 408-A (in the case of audio divider 406-A) or 408-B (in the case of audio divider 406-B). This may be done in any suitable manner. For example, an audio divider 406 may convert an audio input signal 404 from a time domain into a frequency domain, and may then divide the resulting frequency bins into a plurality of frequency domain signals. To this end, each audio divider 406 may include one or more components configured to process the respective audio input signal in accordance with a Discrete Fourier Transform algorithm (e.g., an FFT algorithm). Additionally or alternatively, each audio divider 406 may include a plurality of band-pass filters each configured to pass energy associated with different portions of the audio spectrum. As such, the energy passed by each band-pass filter may correspond to a different frequency channel or band and to a different spectral input signal 408.

Each audio divider 406 may be configured to divide the respective audio input signals 404 into any number of spectral input signals 408 as may serve a particular application. Moreover, as mentioned above, each audio input signal 404 may be divided into spectral input signals 408 that correspond to any suitable types of frequency bands. For instance, in some examples, the total number of spectral input signals 408 derived from one audio input signal 404 may be equal to a total number of stimulation channels by way of which electrical stimulation representative of the audio input signal is to be applied to the recipient, and each spectral input signal 408 may be associated with a respective stimulation channel. In other examples, the total number of spectral input signals 408 derived from one audio input signal 404 may be equal to a total number of frequency bins (e.g., FFT bins) resulting from an application of an FFT algorithm to the audio input signal, and each spectral input signal 408 may correspond to a particular (i.e., single) frequency bin in the plurality of frequency bins resulting from the application of the FFT algorithm. In yet other examples, the total number of frequency domain signals may be greater than the number of stimulation channels but less than the total number of frequency bins resulting from the application of the FFT algorithm. As such, each spectral input signal 408 may correspond to a frequency-contiguous set of frequency bins (i.e., FFT bins that are positioned adjacently or contiguously with respect to the audio spectrum) and may represent an average spectral energy of all of the frequency bins in the frequency-contiguous set of frequency bins.

Figure 5A:
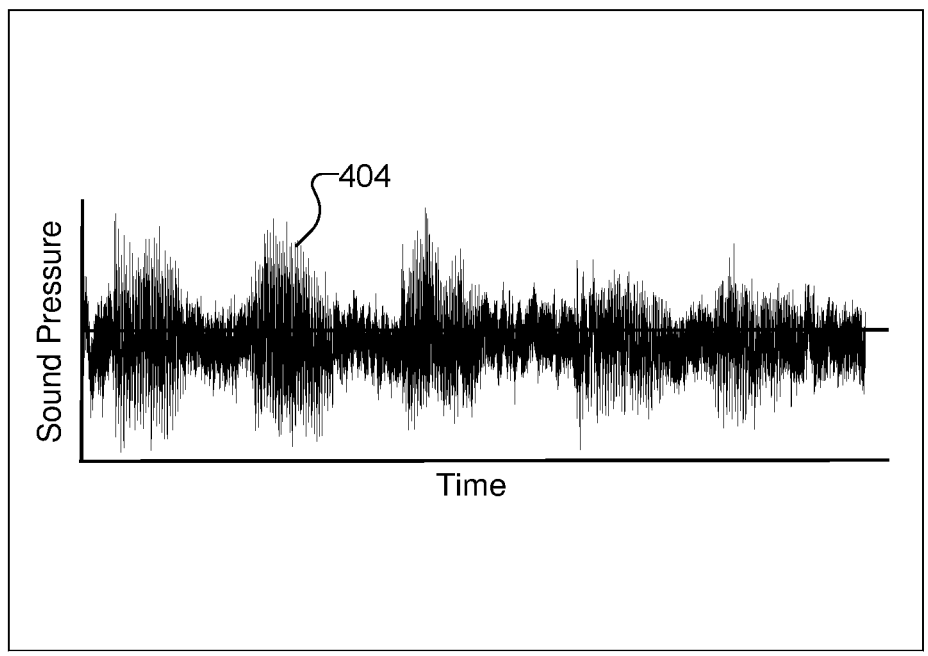
FIG. 5A illustrates an exemplary implementation of an audio input signal received by the sound processor of FIG. 3 according to principles described herein.

To illustrate the function of an audio divider 406, FIG. 5A shows an exemplary implementation of one of audio input signals 404, which will be understood to represent either of audio input signals 404-A or 404-B, or to represent another suitable audio input signal received by one of audio dividers 406 in sound processor 300. As shown, the sound pressure detected by the audio input device capturing the audio input signal 404 may vary in time in accordance with sounds presented to the recipient such that audio input signal 404 is received as an analog, time-domain audio signal. By processing (e.g., dividing) audio input signal 404 as described above, spectral input signals 408 may be generated, as shown in FIG. 5B.

Figure 5B:
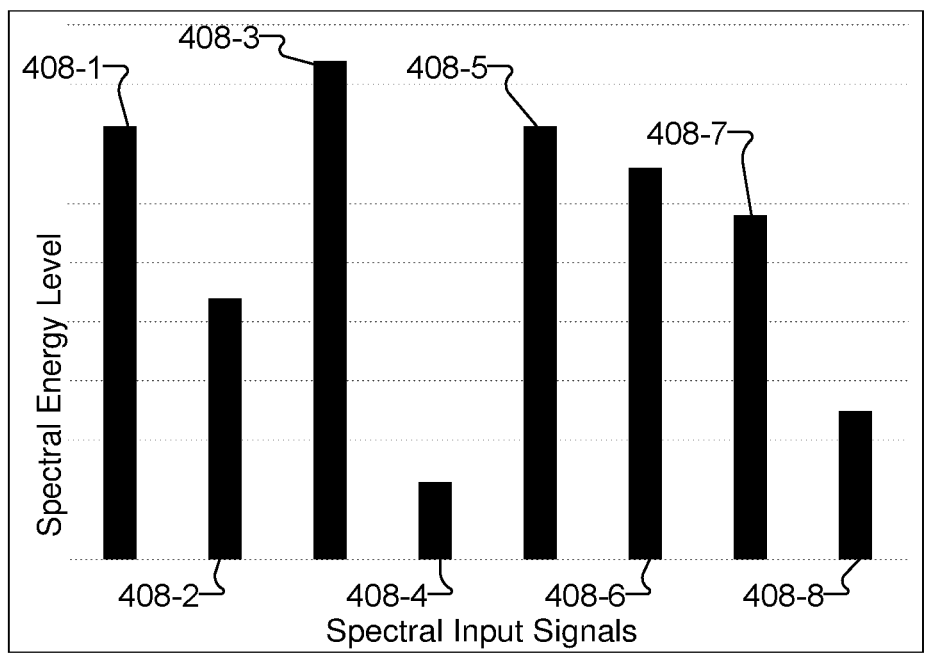
FIG. 5B illustrates an exemplary plurality of frequency domain spectral signals that may be generated by the sound processor of FIG. 3 based on the audio input signal of FIG. 5A according to principles described herein.

Specifically, FIG. 5B illustrates an exemplary plurality of frequency-domain spectral signals (i.e., spectral input signals 408-1 through 408-8) that may be generated by the audio divider 406 based on the audio input signal 404 received (e.g., by processing the audio input signal 404 in accordance with an FFT algorithm). While eight spectral input signals 408 (i.e., spectral input signals 408-1 through 408-8) are explicitly shown in FIG. 5B, it will be understood that the audio input signal 404 may be divided into additional or fewer spectral input signals (e.g., up to a number N of spectral input signals, as shown in FIG. 4) in certain implementations.

Additionally, while frequencies are not explicitly labeled in FIG. 5B, it will be understood that each of spectral input signals 408 may correspond to a particular frequency range. For instance, in certain implementations, as mentioned above, each of spectral input signals 408-1 through 408-8 may correspond to a particular frequency bin (i.e., a single FFT bin) included in a plurality of frequency bins associated with the applied FFT algorithm. In these implementations, a relatively large number of spectral input signals 408 may each be associated with a relatively small portion of the audio spectrum, allowing sound processor 300 to prevent system noise generated by cochlear implant system 100 with relatively precise control and a relatively high resolution. In other words, by dividing each audio input signal 404 into a relatively large number of spectral input signals each corresponding with a relatively small frequency band, sound processor 300 may be able to include and exclude different spectral input signals 408 with a greater degree of precision than in an implementation using fewer spectral input signals corresponding with larger frequency bands. As such, electrical stimulation representative of system noise may be prevented from being applied to a recipient using cochlear implant system 100 with a minimal effect on desirable spectral energy at frequencies surrounding those that are dominated by system noise.

In other implementations, as mentioned above, each of spectral input signals 408-1 through 408-8 may correspond to a respective stimulation channel of cochlear implant system 100 (i.e., the stimulation channels through which electrical stimulation representative of the audio input signal may be applied to the cochlear implant recipient by way of cochlear implant 108). In this type of implementation, there may be fewer spectral energy signals 408 needed to cover the entire audio spectrum, resulting in lower processing requirements, fewer required processing resources, and, as a result, a simpler design and/or a reduced cost. While electrical stimulation representative of system noise may not be prevented from being applied to the recipient with the same degree of precision in these examples as in those implementations described above where spectral input signals 408 correspond to individual FFT bins, the resolution with which system noise can be screened in these examples may be determined to still be sufficiently high to provide a significant benefit to the recipient. As such, a lower cost and simpler design of sound processor 300 may be a valuable tradeoff for the diminished degree of precision provided by a larger number of spectral input signals 408 corresponding to smaller frequency bands.

As mentioned above, in yet other examples, spectral input signals 408 may correspond to frequency bands wider than a single FFT bin but still narrower than an entire stimulation channel to target some mix of both benefits described above (i.e., the high precision and quality of noise prevention and the low system complexity and cost). For instance, each spectral input signal 408 may correspond to an average of a frequency-contiguous set of frequency bins (i.e., a consecutive group of FFT bins) included in a plurality of frequency bins associated with the FFT algorithm applied to each audio input signal 404.

As shown in FIG. 5B, while individual spectral input signals 408 are drawn along the x-axis, the y-axis indicates a relative spectral energy level of the spectral input signals 408. Thus, it may be seen that certain spectral input signals 408 representative of certain frequency bands (e.g., the frequency band corresponding to spectral input signal 408-4) have lower spectral energy levels than other spectral input signals 408 representative of other frequency bands (e.g., the frequency band corresponding to spectral input signal 408-3).

As will be described in more detail below, when a spectral input signal 408 has a spectral energy level below a predetermined system noise threshold for an associated frequency band, the spectral input signal 408 may be determined to be dominated by system noise. In other words, while the spectral input signal 408 may contain useful information regarding an audio input signal 404, it may be determined that the useful information is masked by the system noise to a significant extent. As a result, it may be beneficial for sound processor 300 to detect and react to system noise generated by cochlear implant system 100 in one of the ways described herein.

Returning to FIG. 4, each spectral input signal 408 may serve as an input to a respective spectral noise management system 410, as shown. After spectral input signals 408 have been generated (i.e., by the dividing up of audio input signals 404 by audio dividers 406), each spectral noise management system 410 may perform one or more of the other operations described above in connection with noise management facility 302. Specifically, for example, in the case of spectral noise management system 410-A1 receiving spectral input signal 408-A1 as an input, spectral noise management system 410-A1 may determine whether a spectral energy level of spectral input signal 408-A1 exceeds a predetermined system noise threshold (e.g., a system noise threshold based on a characterization of system noise generated by cochlear implant system 100 within the frequency band to which spectral input signal 408-A1 correlates), and may perform, based on that determination, an action that impacts stimulation provided to the recipient. For example, spectral noise management system 410-A1 may generate spectral output signal 412-A1 by including spectral input signal 408-A1 in spectral output signal 412-A1 (i.e., passing spectral input signal 408-A1 through) if the spectral energy level exceeds the predetermined system noise threshold, and by excluding spectral input signal 408-A1 from spectral output signal 412-A1 (i.e., filtering or replacing spectral input signal 408-A1) if the spectral energy level does not exceed the predetermined system noise threshold. As another example, spectral noise management system 410-A1 may generate noise indicator signal 414-A1 for use (e.g., by signal output facility 416) in detecting a toggling off or on of audio input device 402-A and revising (in response to the detection of the toggling) a particular dynamic weighting factor assigned to audio input signal 404-A in accordance with the examples such as those described above (e.g., to deemphasize audio capture from the remote microphone when the speech is over, to emphasize audio capture from the local microphone when someone whispers in the recipient's ear during the speech, etc.) or with a variety of other possible scenarios.

Figure 6:
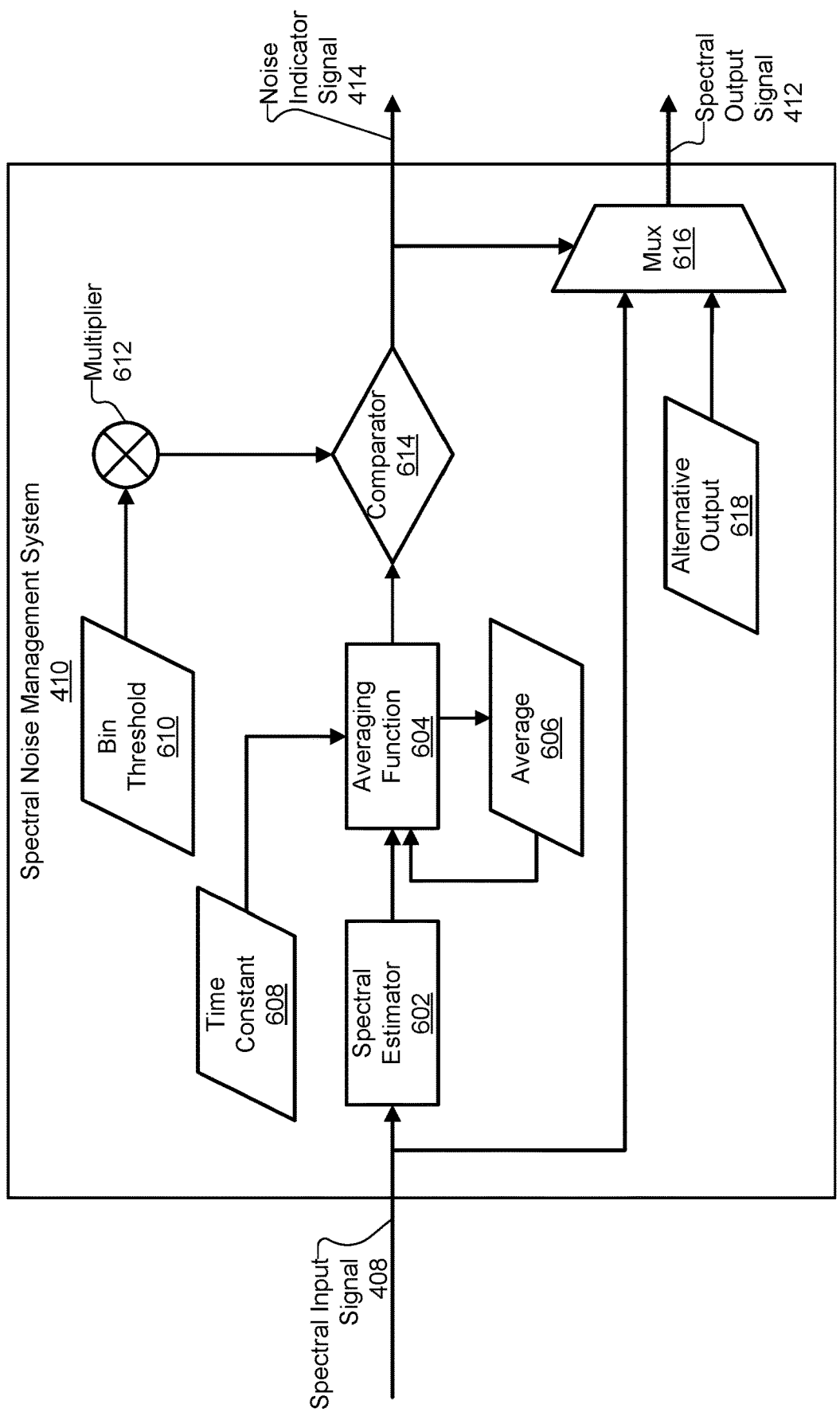
FIG. 6 illustrates an exemplary implementation of a spectral noise management system according to principles described herein.

FIG. 6 illustrates an exemplary implementation of one of spectral noise management systems 410 (i.e., an exemplary implementation of any of spectral noise management systems 410-A1 through 410-B3 in FIG. 4). As shown in FIG. 6, spectral noise management system 410 may include a spectral estimator 602, an averaging function 604, an average 606, a time constant 608, a bin threshold 610, a multiplier 612, a comparator 614, a signal output selector 616 (labeled "mux 616"), and an alternative output 618. It will be recognized that the components shown in FIG. 6 are merely representative of the many different components that may be included in spectral noise management system 410, and that spectral noise management system 410 may include additional or alternative components as may serve a particular implementation. In some implementations, the components of spectral noise management system 410 may be implemented entirely in hardware, entirely in software, and/or using a combination of both hardware and software. Each of these components associated with spectral noise management system 410 will now be described.

Spectral input signal 408 (e.g., one of spectral input signals 408-A1 through 408-B3 illustrated in FIG. 4) may be received by spectral noise management system 410 from one of audio dividers 406. More specifically, as shown, spectral input signal 408 may be input into spectral estimator 602.

Spectral estimator 602 may be configured to measure, estimate, or otherwise determine an energy level of spectral input signal 408 in any suitable way. For example, spectral estimator 602 may calculate the energy level of spectral input signal 408 to be a sum of a square of a real part of the particular spectral input signal 408 and a square of an imaginary part of spectral input signal 408. Accordingly, if P[n] represents the spectral energy level of spectral input signal 408 (i.e., where P is a spectral energy level function of an index, n, that represents a particular spectral input signal, in this case spectral input signal 408), FFTr[n] represents a real portion of spectral input signal 408, and FFTi[n] represents an imaginary portion of spectral input signal 408, spectral estimator 602 may calculate the spectral energy level of spectral input signal 408 in accordance with:

$$P[n] = FFTi[n]^2 + FFTr[n]^2$$

Spectral noise management system 410 may then input the determined spectral energy level of spectral input signal 408 (i.e., the calculated result, P[n]) into averaging function 604.

Averaging function 604 may determine an average spectral energy level of spectral input signal 408 over a period of time. Averaging function 604 may determine the average spectral energy level of spectral input signal 408 over the period of time in any suitable way. For example, in some implementations, averaging function 604 may apply an exponential moving average smoothing function to the determined energy level of spectral input signal 408 (e.g., the calculated result, P[n], received from spectral estimator 602) to determine an average spectral energy level of spectral input signal 408 over the period of time. Average 606 may include or be associated with data stored in memory or within a storage facility (e.g., storage facility 304) that is representative of a temporal average of past observations and/or measurements of the energy level of spectral input signal 408 (e.g., measured amounts of spectral energy measured by spectral estimator 602 at different times prior to the measuring of spectral input signal 408). Averaging function 604 may apply the exponential moving average function to determine the energy level of spectral input signal 408 with average 606 to determine an average spectral energy level of spectral input signal 408 over the period of time.

For example, if x[n] represents the determined average spectral energy level of spectral input signal 408, and α represents a smoothing factor between 0 and 1 (i.e., such that 0<α<1), an exponential moving average smoothing function may be expressed as:

$$x[n]=((1-\alpha) \times P[n])+(\alpha \times x[n])$$

Averaging function 604 may utilize time constant 608 in order to select a suitable value for α. Thus, for example, averaging function 604 may calculate a running average of the spectral energy of spectral input signal 408 that goes back a certain amount in time based on time constant 608. In some examples, time constant 608 may include or be associated with data stored in memory or within a storage facility (e.g., storage facility 304) and may be representative of a suitable smoothing time interval. As such, the output of averaging function 604 (i.e., the determined average spectral energy level of spectral input signal 408, x[n]) may be less susceptible to incorporating fast but temporary changes to spectral input signal 408 that could cause glitchy or unsmooth application of stimulation to the recipient. To this end, in some implementations, time constant 608 may be selected in a range between approximately 20 milliseconds and approximately 30 milliseconds (e.g., 25 milliseconds). Such a time constant may ensure that spectral noise management system 410 can be responsive to relatively significant changes in spectral input signal 408 (e.g., when the spectral energy level of spectral input signal 408 increases to remain above the predetermined system noise threshold for a non-trivial period of time, when the spectral energy level decreases to remain below the predetermined system noise threshold for a non-trivial period of time, etc.), while disregarding trivial changes that are more short-lived and could cause a degradation in quality perceived by the recipient by, for example, causing stimulation associated with spectral input signal 408 to quickly shut on and off in a glitchy fashion.

In one implementation, where $F_s$ represents a sample rate of cochlear implant system 100 (e.g., of sound processor 300), t represents smoothing time constant 608, and UpdateInterval represents the number of samples between FFT updates, sound processor 300 (e.g., averaging function 604) may select α in accordance with:

$$\alpha=e^{-UpdateInterval/(t \times Fs)}$$

Upon determining an average energy level of spectral input signal 408 over the period of time, averaging function 604 may update average 606 such that averaging function 604 will continuously output a recursive average energy level (i.e., an average energy level that is determined based on previous averages that are determined based on yet other previous averages, and so forth). Averaging function 604 may also output the determined average energy level of spectral input signal 408 to comparator 614, as shown.

Bin threshold 610 may include or be associated with data stored in memory or in a storage facility (e.g., storage facility 304) and that represents a suitable system noise threshold that is associated with the particular portion of the audio spectrum with which spectral input signal 408 is associated. For example, when spectral input signal 408 is associated with a portion of an audio spectrum from 5.0 kHz to 5.2 kHz, bin threshold 610 may include data representative of a predetermined system noise threshold that also corresponds to the portion of the audio spectrum from 5.0 kHz to 5.2 kHz. As mentioned above, in certain examples, the predetermined system noise threshold of bin threshold 610 may be accessed from memory or storage (e.g., by way of a look up table or the like).

The system noise threshold may be predetermined (i.e., originally determined prior to being stored in the memory or storage facility for access by spectral noise management system 410) by sound processor 300 (e.g., noise management facility 302) or by another system (e.g., a test sound processor system representative of sound processor 300 and other sound processors that are to be manufactured and configured equivalently or similarly) in any way as may serve a particular implementation.

Figure 7:
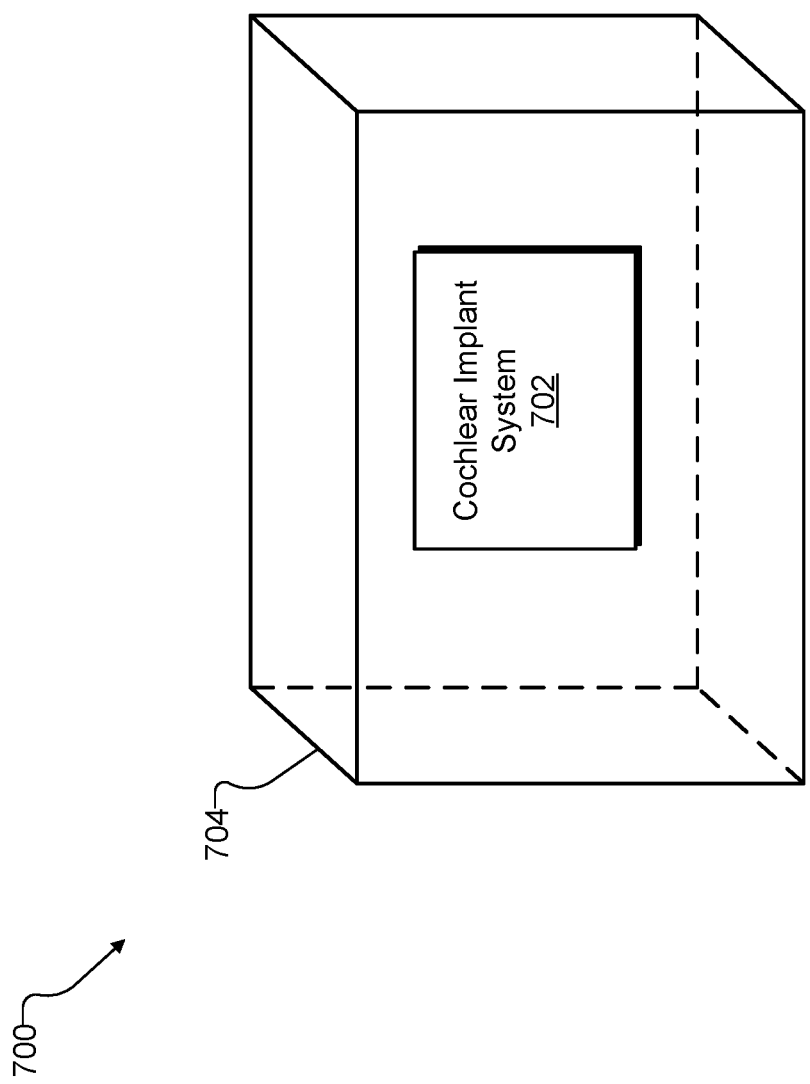
FIG. 7 illustrates an exemplary configuration in which the cochlear implant system of FIG. 1 is used to determine a predetermined system noise threshold according to principles described herein.

To illustrate, FIG. 7 shows an exemplary configuration 700 in which a cochlear implant system 702 is used to determine the predetermined system noise threshold. In this example, cochlear implant system 702 may be the same or similar as cochlear implant system 100 and, as such, may include a sound processor that is the same or similar to sound processor 300 as described above. In certain examples, cochlear implant system 100 may implement cochlear implant system 702, while, in other examples, cochlear implant system 702 may be implemented by, for example, a test cochlear implant system used by a manufacturer of cochlear implant system 100 to characterize system noise of cochlear implant system 702 and/or the sound processor included therein. For instance, the sound processor within cochlear implant system 702 may be a sound processor having similar system noise characteristics as sound processor 300 (e.g., a sound processor that is the same model and uses the same configuration of audio input device, pulse rate, etc., as sound processor 300) such that predetermined system noise thresholds determined with respect to cochlear implant system 702 and the sound processor included therein may apply to other cochlear implant systems and sound processors such as cochlear implant system 100 and sound processor 300.

As shown in configuration 700, cochlear implant system 702 may be placed within an anechoic chamber 704 (e.g., a certified sound pressure level booth below 20 dBHL). Anechoic chamber 704 may be any environment within which a cochlear implant system (e.g., cochlear implant system 702) may be placed and within which an acoustic and/or electromagnetic environment surrounding cochlear implant system 702 may be controlled (e.g., so as to reduce sources of noise other than system noise generated by the cochlear implant system). For example, anechoic chamber 704 may be configured such that, when cochlear implant system 702 is placed within anechoic chamber 704, cochlear implant system 702 may be isolated (e.g., totally or partially) from exterior sources of acoustic noise, electromagnetic noise (e.g., RF noise), and/or other types of environmental noise such that only system noise generated by cochlear implant system 702 may be present. In this quiet environment the spectral bands of the noise floor can be determined by sampling the output of the moving average. These sampled values can then be used to determine the mean of the noise and its variance.

While cochlear implant system 702 is located within anechoic chamber 704, one or more components of cochlear implant system 702 (e.g., the sound processor included within cochlear implant system 702) may receive a test frequency domain signal representative of system noise within a particular frequency band. Because useful information included within the test frequency domain signal is controlled (e.g., by being known precisely, by being eliminated, etc.), and because various sources of environmental noise (e.g., acoustic noise, electromagnetic noise, etc.) are similarly controlled, the spectral energy within the test frequency domain signal representative of system noise of cochlear implant system 702 may be determined with a relatively high degree of precision. For example, the sound processor included within cochlear implant system 702 may determine an amplitude of the test frequency domain signal and may set the predetermined system noise threshold to a value within a predetermined amount of (e.g., slightly higher than) the determined amplitude of the test frequency domain.

In some examples, while cochlear implant system 702 is located within anechoic chamber 704, the sound processor included within cochlear implant system 702 may activate the audio input device of cochlear implant system 702, and may receive the test frequency domain signal by way of the audio input device. The test frequency domain signal may be representative of system noise (e.g., acoustic noise and/or electromagnetic noise) generated by or otherwise associated with cochlear implant system 702 within the frequency band, and received by the audio input device while cochlear implant system 702 is located within anechoic chamber 704.

A test frequency domain signal received by way of the audio input device while cochlear implant system 702 is located within (e.g., isolated from external noise within) anechoic chamber 704 may include only information representative of system noise (e.g., acoustic and/or electrical noise generated by cochlear implant system 702) within the frequency band, or may include information representative of the system noise along with information representative of controlled noise or signals that may be subtracted from the test frequency domain signal to determine the amplitude of the system noise. The sound processor may receive the test frequency domain signal and/or determine the energy level of the test frequency domain signal in any of the ways described herein.

Returning to FIG. 6, sound processor 300 (e.g., spectral noise management system 410) may additionally or alternatively determine the predetermined system noise threshold associated with bin threshold 610 based on any other suitable criteria, including, for example, a variance of an average amplitude of spectral energy contained within the test frequency domain signal, a pulse rate of the cochlear implant system (e.g., cochlear implant system 702), a sample rate of the test frequency domain signal, and/or an FFT update rate of the frequency domain signal. Thus, in order for cochlear implant system 702 and the sound processor included therein to fairly represent the system noise generated by cochlear implant system 100 and sound processor 300, each of these factors may be equivalent or similar in both cochlear implant systems 702 and 100.

In some examples, sound processor 300 may store and/or access at least one system noise threshold (e.g., a system noise threshold associated with bin threshold 610) from a noise profile. As used herein, a "noise profile" may be any suitable data structure that includes data representative of at least one system noise threshold associated with a particular configuration of a cochlear implant system. A noise profile may include information regarding any configurable option of a cochlear implant system, including, but not limited to, a hardware configuration (e.g., a particular audio input device coupled to the cochlear implant system), an FFT update rate, a pulse rate, a sample rate, and/or any other such options as may serve a particular implementation.

By way of illustration, cochlear implant system 100 may be configured with a first audio input device (e.g., a T-MIC™ microphone from Advanced Bionics). While in this configuration, cochlear implant system 100 may be associated with a first noise profile that includes a first set of system noise thresholds. A different implementation of cochlear implant system 100 may be configured with a second audio input device (e.g., a BTE microphone) instead of the first audio input device. For example, a different recipient with a different cochlear implant system may prefer the second audio input device, or the recipient using the first implementation of cochlear implant system 100 may switch out the first audio input device to use the second audio input device. While in this alternative configuration, cochlear implant system 100 may be associated with a second noise profile that includes a second set of system noise thresholds. Additionally or alternatively, the implementation of cochlear implant system 100 may include a sound processor such as sound processor 300, which receives audio input signals 404 from a plurality of audio input devices 402, and cochlear implant system 100 may access both noise profiles associated with both audio input devices. In this way, any configuration of cochlear implant system 100 may be associated with one or more suitable noise profiles.

Figure 8A:
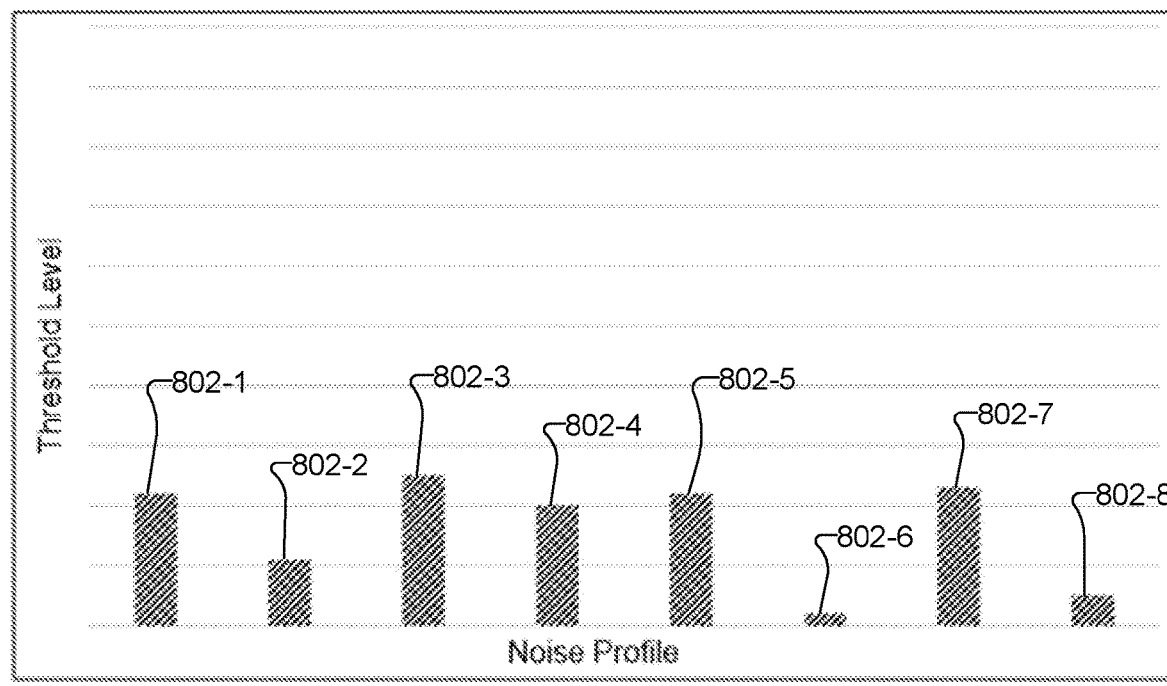
FIG. 8A illustrates an exemplary noise profile associated with a particular configuration of the cochlear implant system of FIG. 1 according to principles described herein.

To illustrate, FIG. 8A shows an exemplary noise profile associated with a particular configuration of cochlear implant system 100. As shown, the noise profile of FIG. 8A may include a plurality of system noise thresholds 802 (e.g., system noise thresholds 802-1 through 802-8) each associated with different respective frequency bands (e.g., 20 Hz to 100 Hz, 5.0 kHz to 5.2 kHz, 10 kHz to 15 kHz, etc.). As described above, system noise thresholds 802 may be originally determined (i.e., predetermined) by measuring system noise in a configuration such as configuration 700 of FIG. 7 for a cochlear implant system such as cochlear implant system 100 or a test cochlear implant system such as cochlear implant system 702. Then, in operation, sound processor 300 may determine the system noise thresholds 802 for the particular configuration of cochlear implant system 100 by, for example, accessing data representative of the noise profile associated with the particular configuration of cochlear implant system 100 from a lookup table or the like stored in storage facility 304.

In some implementations, sound processor 300 may access data representative of a noise profile from a library of noise profiles. A library of noise profiles may include a plurality of noise profiles that are each associated with a different respective configuration of a cochlear implant system. For example, a library of noise profiles may include one or more noise profiles associated with a particular cochlear implant system (e.g., cochlear implant system 100) as well as one or more noise profiles associated with other particular cochlear implant systems (e.g., different implementations of cochlear implant system 100).

Each noise profile included in the library of noise profiles may be associated with a different configuration of the particular cochlear implant system. For example, a library of noise profiles associated with cochlear implant system 100 may include a first noise profile associated with a configuration of cochlear implant system 100 wherein an audio input device 402 is a T-MIC™ microphone from Advanced Bionics, and cochlear implant system 100 is associated with a pulse rate of 1,856 Hz. The library of noise profiles associated with cochlear implant system 100 may also include a second noise profile associated with a configuration of cochlear implant system 100 where the audio input device 402 is a BTE microphone, and cochlear implant system 100 is associated with a pulse rate of 1,954 Hz. The library of noise profiles may include any number of other noise profiles associated with one or more alternative configurations of cochlear implant system 100. Such other noise profiles may include any suitable information that may be related to any variation in a predetermined system noise threshold of cochlear implant system 100. Such information may include, but is not limited to, a hardware configuration of cochlear implant system 100, an FFT update rate associated with cochlear implant system 100, a pulse rate associated with cochlear implant system 100, a sample rate associated with cochlear implant system 100, and the like.

Sound processor 300 may receive input representative of a selection of a noise profile and may access, based on the received input, the selected noise profile. Sound processor 300 may receive input representative of the selection in any suitable way. For example, cochlear implant system 100 may provide a user interface that allows a user to select a particular noise profile from the library of noise profiles, or to input various criteria that cochlear implant system 100 may use to select an appropriate noise profile. Additionally or alternatively, sound processor 300 may automatically determine a configuration of a cochlear implant system (i.e., automatically determine various relevant characteristics of the cochlear implant system), and select, based on the determined configuration, a noise profile from the library of noise profiles.

For instance, referring to the example of FIG. 6, sound processor 300 may determine a system noise threshold for spectral input signal 408 (i.e., the system noise threshold associated with bin threshold 610) by determining that cochlear implant system 100 is configured with a T-MIC™ microphone from Advanced Bionics and is associated with a pulse rate of 1,854 Hz, and by selecting the first noise profile based on that determination. Sound processor 300 may then determine system noise threshold 802 for cochlear implant system 100 by accessing, based on the selection of the first noise profile, data representative of the first noise profile included in the library of noise profiles.

Returning to FIG. 6, data representative of bin threshold 610 is passed to multiplier 612. Multiplier 612 may be configured to adjust bin threshold 610 in any suitable way. For example, multiplier 612 may (e.g., as directed by sound processor 300) adjust bin threshold 610 such that bin threshold 610 is set slightly above a measured system noise threshold in order to avoid "fluttering" in quiet environments. Additionally or alternatively, multiplier 612 may be configured to compensate for adaptive gain control ("AGC") that may be applied to spectral input signal 408 at an earlier stage in the processes of sound processor 300 (e.g., by one of audio input device 402, by one of audio dividers 406, etc.). Multiplier 612 may then pass adjusted bin threshold 610 to comparator 614.

As shown, comparator 614 compares the output of averaging function 604 with adjusted bin threshold 610. Comparator 614 may perform this comparison in any suitable way. For example, comparator 614 may compare an energy level value that corresponds to the output of averaging function 604 with an energy level value that corresponds with adjusted bin threshold 610. In this way, comparator 614 may determine whether the output of averaging function 604 is greater than an adjusted bin threshold 610 (i.e., indicating that spectral input signal 4086 includes a significant amount of useful information that outweighs any system noise included on the signal), or whether the output of averaging function 604 is less than the adjusted bin threshold 610 (i.e., indicating that any useful information that may be included with spectral input signal 408 is effectively masked and rendered useless by system noise included on the signal).

Figure 8B:
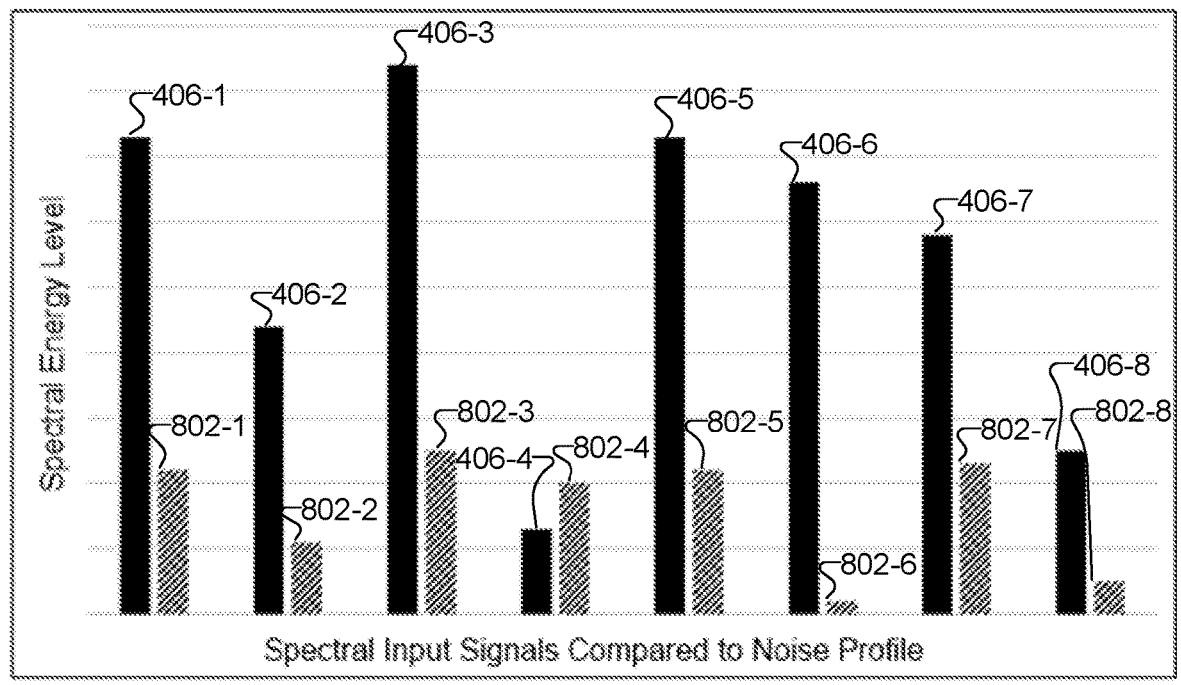
FIG. 8B illustrates exemplary spectral input signals received by the cochlear implant system of FIG. 1 alongside respective system noise thresholds associated with the spectral input signals in the noise profile of FIG. 8A according to principles described herein.

To illustrate an exemplary comparison of a plurality of spectral input signals to an associated plurality of system noise thresholds in a noise profile associated with a configuration of a cochlear implant system, FIG. 8B shows spectral input signals 408 alongside respective system noise thresholds 802 in the noise profile of FIG. 8A. As shown in FIG. 8B, all of spectral input signals 408 have energy levels that exceed (i.e., are greater than) the respective system noise thresholds 802 corresponding to the spectral input signals 408, with the exception of spectral input signal 408-4, which does not exceed (i.e., is less than) system noise threshold 802-4 (i.e., the respective system noise threshold 802 to which spectral input signal 408-4 corresponds). Accordingly, sound processor 300 (e.g., by way of comparator 614 within spectral noise management system 410) may determine that all spectral input signals have energy levels that exceed their associated system noise thresholds with the exception of spectral input signal 408-4, which sound processor 300 may determine does not exceed its corresponding system noise threshold (i.e., system noise threshold 802-4).

As such, returning to FIG. 6, comparator 614 may output a signal that indicates a result of the comparison between the output of averaging function 604 and the adjusted bin threshold 610 to signal output selector 616. For example, comparator 614 may determine that the output of averaging function 604 is greater than adjusted bin threshold 610. If comparator 614 determines that the output of averaging function 604 is greater than adjusted bin threshold 610, comparator 614 may output a signal to signal output selector 616 that indicates that the output of averaging function 604 is greater than adjusted bin threshold 610. If comparator 614 determines that the output of averaging function 604 is not greater than (e.g., is less than or equal to) adjusted bin threshold 610, comparator 614 may output a signal to signal output selector 616 that indicates that the output of averaging function 604 is not greater than adjusted bin threshold 610.

Signal output selector 616 may be configured to generate spectral output signal 412 based on the select signal received from comparator 614. For example, as shown in FIG. 6, signal output selector 616 may be implemented as a multiplexer ("mux") that receives a select signal from comparator 614, and receives input signals including spectral input signal 408 and alternative output 618. When the select signal from comparator 614 indicates that the output of averaging function 604 exceeds adjusted bin threshold 610 (i.e., indicating that spectral input signal 408 includes useful information that is not overwhelmed and/or masked by system noise), signal output selector 616 may generate spectral output signal 412 by including spectral input signal 408 in spectral output signal 412 (e.g., by outputting or passing through spectral input signal 408 as is). Additionally or alternatively, when the signal from comparator 614 indicates that the output of averaging function 604 does not exceed adjusted bin threshold 610 (i.e., indicating that any useful information included within spectral input signal 408 is effectively masked or overwhelmed by system noise), signal output selector 616 may generate spectral output signal 412 by excluding spectral input signal 408 from spectral output signal 412 (e.g., by replacing spectral input signal 408 with alternative output 618, as described below). In this way, sound processor 300 may generate spectral output signal 412 by including spectral input signal 408 in spectral output signal 412 if the output of averaging function 604 exceeds adjusted bin threshold 610, and excluding spectral input signal 408 from spectral output signal 412 if the output of averaging function 604 does not exceed adjusted bin threshold 610.

In some instances, such as where signal output selector 616 excludes spectral input signal 408 from spectral output signal 412, signal output selector 616 may include alternative output 618 (i.e., an alternative output signal) in spectral output signal 412. Alternative output 618 may represent any suitable frequency domain signal that corresponds to a frequency range associated with spectral input signal 408. For example, alternative output 618 may include a frequency domain signal that corresponds to the frequency range associated with spectral input signal 408 and that represents a spectral energy level with a null value for the frequency range associated with spectral input signal 408. This may be referred to as "zeroing out" a frequency range (e.g., an FFT bin, a stimulation channel, etc.) associated with spectral input signal 408.

For example, FIG. 9 illustrates spectral output signals 412 that may be generated by sound processor 300 (e.g., by way of spectral noise management systems 410) to react to system noise generated by a cochlear implant system. Specifically, FIG. 9 shows spectral output signals 412 generated based on a comparison of spectral input signals 408 and system noise thresholds 802 as illustrated in FIG. 8B. As shown, most of spectral output signals 412 are equivalent to (e.g., correspond to the same frequency range and have the same energy levels as) spectral input signals 408 illustrated in FIGS. 5B and 8B. This is because most of spectral input signals 408 exceed their respective system noise thresholds 802 (as shown in FIG. 8B) such that most of spectral input signals 408 have been included in their respective spectral output signals 412 (i.e., passed through). An exception to this is illustrated by spectral output signal 412-4. As illustrated in FIG. 8B, spectral input signal 408-4 does not exceed system noise threshold 802-4. Hence, sound processor 300 (e.g., by way of spectral noise management system 410-4) generates spectral output signal 412-4 (i.e., the spectral output signal 412 corresponding to the frequency range of spectral input signal 408-4) to have a null spectral energy value (e.g., −100 dB). In other words, sound processor 300 excludes spectral input signal 408-4 from spectral output signal 412-4 and instead includes a respective alternative output signal 618 (which, in this case, is a null spectral energy value).

While spectral output signal 412-4 illustrates a null spectral energy value (e.g., −100 dB), it will be understood that alternative output 618 may, in certain implementations, include a non-null spectral energy value (e.g., a value greater than −100 dB). For example, alternative output 618 may include a "comfort noise" signal. As used herein, "comfort noise" or a "comfort noise signal" may be any non-null frequency domain signal that sound processor 300 may substitute for spectral input signal 408 in spectral output signal 412 when spectral input signal 408 does not exceed adjusted bin threshold 610. Comfort noise may be used due to discomfort or other undesirable effects that null values for alternative output 618 may cause a recipient to experience. As such, in certain examples, comfort noise may include artificially generated noise (i.e., not including useful information from a respective spectral input signal 408) at a spectral energy low enough to not distract the user from useful information carried by other spectral input signals but high enough to not cause discomfort. In other examples, a comfort noise signal may include a frequency domain signal that is representative of spectral input signal 408 (e.g., both system noise and useful information included within spectral input signal 408), but may be generated with an energy level reduced by a predetermined factor (e.g., 0.5, 0.1, etc.).

Accordingly, returning to FIG. 6, signal output selector 616 may receive a signal from comparator 614 that indicates that the output of averaging function 604 does not exceed adjusted bin threshold 610. In response, signal output selector 616 may generate spectral output signal 412 by including alternative output 618 in place of spectral input signal 408. As described above, alternative output 618 may include a spectral signal representative of comfort noise. In this way, sound processor 300 (e.g., by way of signal output selector 616) may generate spectral output signal 412 by including a spectral signal representative of comfort noise in place of spectral input signal 408.

Although not pictured in FIG. 6, in some implementations, signal output selector 616 may generate a spectral output signal 412 based on whether one or more other spectral input signals (e.g., one or more "nearest neighbor" bins) also exceed one or more other associated predetermined system noise thresholds. For example, if the spectral noise management system 410 illustrated in FIG. 6 is spectral noise management system 410-1, a signal output selector 616 associated with spectral noise management system 410-2 (i.e., associated with an adjacent frequency band to the frequency band with which spectral noise management system 410-1 is associated) may be configured to "zero out" spectral input signal 408-2 only when all of spectral input signals 408-1 through 408-3 do not exceed their associated predetermined system noise thresholds.

As mentioned above, one action to impact the stimulation provided to the recipient that may be performed by sound processor 300 is to generate spectral output signals 412 based on the determination of whether the spectral energy level of spectral input signal 408 exceeds the predetermined system noise threshold by including or excluding spectral input signal 408 in spectral output signal 412. This may impact the stimulation provided to the recipient because sound processor 300 may use any or all of spectral output signals 412 (e.g., including spectral output signals 412-1 through 412-8 illustrated in FIG. 9) to generate a stimulation waveform that may be communicated to the cochlear implant by way of one or more components of the cochlear implant system that includes the cochlear implant (e.g., one or more components of cochlear implant system 100). The cochlear implant may then provide electrical stimulation to the recipient by way of one or more electrodes (e.g., electrodes 112) in accordance with (e.g., based on) the generated stimulation waveform.

Figure 10:
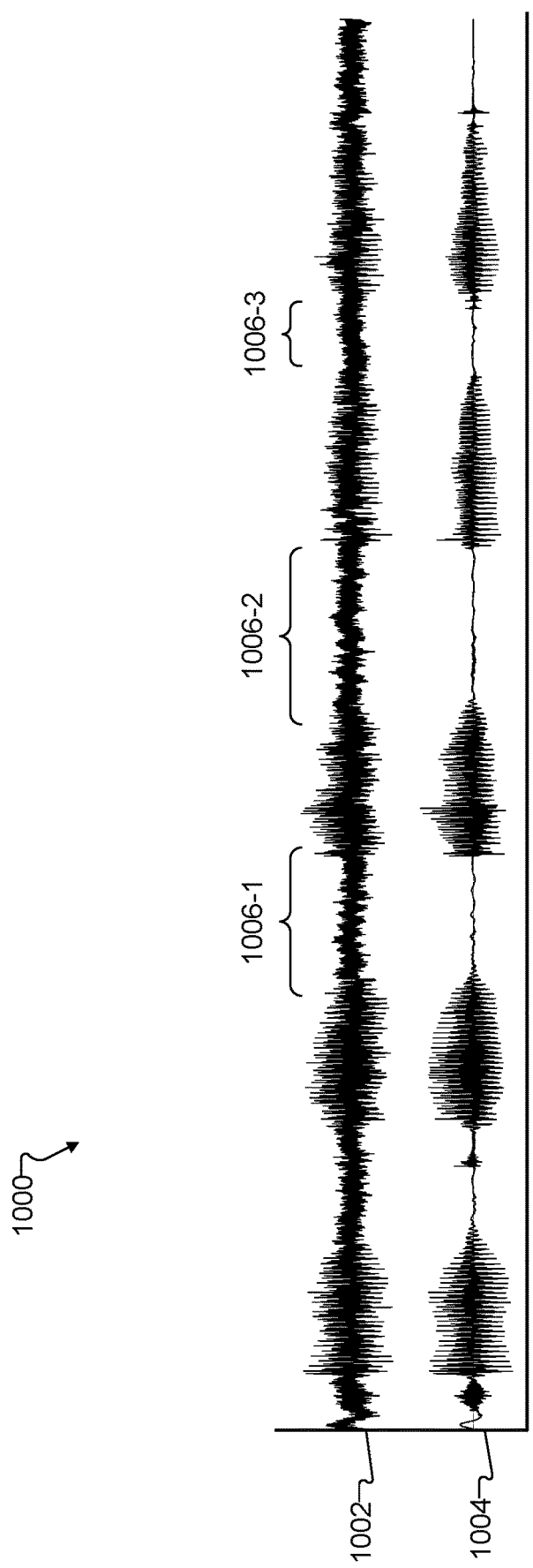
FIG. 10 illustrates exemplary electrical stimulation waveforms generated for application to a recipient according to principles described herein.

To illustrate, FIG. 10 shows a set of exemplary electrical stimulation waveforms generated for application to a recipient. In particular, stimulation waveform 1002 corresponds to an electrical stimulation waveform that a conventional sound processor may generate when presented with acoustic stimulation (e.g., a quiet sound). In contrast, stimulation waveform 1004 shows an electrical stimulation waveform that a sound processor configured as described herein (e.g., sound processor 300) may generate, in accordance with the systems and methods described herein, when presented with the same acoustic stimulation. As shown, stimulation waveform 1004 may be similar to stimulation waveform 1002, but with a significant amount of noise (e.g., system noise) removed from the stimulation waveform 1004. Specifically, waveform segments 1006 (i.e., segments 1006-1 through 1006-3) indicate specific portions of stimulation waveforms 1002 and 1004 where significant amounts of noise present in stimulation waveform 1002 have been removed from stimulation waveform 1004. As described above, by reducing system noise in this way, a cochlear implant system may make it easier for the recipient to perceive sounds (e.g., to understand voices, etc.) particularly in quiet places. For example, if both stimulations waveforms 1002 and 1004 represent the sound of someone speaking quietly in a quiet room, it may be easier for the recipient to perceive and understand the quiet speech by being presented with stimulation waveform 1004 than by being presented with stimulation waveform 1004.

Returning to FIG. 6, spectral noise management system 410 may generate noise indicator signal 414 based on the determination, made by comparator 614, of whether spectral energy level of spectral input signal 408 exceeds the predetermined system noise threshold. For example, noise indicator signal 414 may be a binary signal assigned a first value if the spectral energy level has been determined to exceed the predetermined system noise threshold and assigned a second value if the spectral energy level has been determined not to exceed the predetermined system noise threshold.

Accordingly, returning to FIG. 4, respective spectral output signals 412 and noise indicator signals 414 may all feed into signal output facility 416, which may perform various functions to generate transmission signal 418. Transmission signal 418 may be transmitted (e.g., by way of headpiece 106 and communication link 114) to cochlear implant 108 for use in applying electrical stimulation (e.g., such as waveform 1004 in FIG. 10) to the recipient. Signal output facility 416 may perform various functions, such as mapping signal levels of the spectral output signals 412 to amplitude signals associated with stimulation channels of a cochlear implant (e.g., cochlear implant 108) that sound processor 300 is configured to direct, signal compression operations, multiplexing operations in which the amplitude signals are serialized (e.g., output one at a time in a continuous round-robin manner), and so forth. As part of these and other functions, and as an addition or an alternative to the action of including or excluding each spectral input signal 408 on each spectral output signal 412, signal output facility 416 may be configured to perform one or more other actions that impact the stimulation provided to the recipient (e.g., by affecting transmission signal 418 as it is generated).

For example, signal output facility 416 may be configured to detect, based on noise indicator signals 414, a toggling off or on of each audio input device 402, and, based on the detection of the toggling, to revise dynamic weighting factors assigned to audio input signals 404 in accordance with what the recipient is likely to want to hear. As used herein, an audio input device 402 may be "toggled off" when the audio input device ceases to capture much or any significant audio data. For example, if the audio input device 402 is a media player playing music or other media content, the media player may be considered to be toggled off when the media content ends and no audio data is being provided by the media device (even if the device is still powered on and/or may begin playing additional media content at any time). As another example, if the audio input device 402 is a microphone into which a person is talking (e.g., the remote microphone being used for the speech or the local microphone being whispered into in the examples described above), the audio input device 402 may be considered to be toggled off when the person ceases talking and only environmental "room" noise is being captured by the microphone (even if the microphone is still active and ready to capture additional voice audio at any time). Similarly, as used herein, an audio input device 402 may be "toggled on" when the audio input device begins capturing significant audio data after a period in which no significant audio data was present. For example, if the media device starts playback of a new instance of media content or a person begins speaking in the microphone of the examples above, these audio input devices may be considered to be dynamically toggled back on (even if they were never powered down, deactivated, or the like).

In some examples, an audio input device 402 may be detected to be toggled off or on based on audio input capture over a period of time. This is because it may be undesirable for weighting factors to be changed frequently and under very dynamic circumstances. For example, referring again to the example scenarios described above, it may be disorienting or irritating to the recipient if audio input signals are remixed during a few seconds of silence between songs when listening to the media player, or when the speaker pauses for a second or two during the speech for dramatic effect. Accordingly, signal output facility 416 may be configured only to detect a toggling off or on of a particular audio input device if audio data or silence continues to be detected over a threshold period of time.

Signal output facility 416 may detect the toggling off or on of the audio input devices in any suitable manner. For example, the detection may be made channel by channel based on each individual noise indicator signal 414, or may be made more globally for the audio input device based on what is indicated by all of the noise indicator signals 414 for a particular audio input device 402 (e.g., all of noise indicator signals 414-A for audio input device 402-A, all of noise indicator signals 414-B for audio input device 402-B, etc.). Additionally, signal output facility 416 may be configured to make a positive detection based on any thresholds or criteria as may serve a particular implementation. For instance, in one implementation, all of noise indicator signals 414-A may need to be in agreement that the predetermined system noise threshold is not exceeded on any channel in order for signal output facility to make a positive detection that audio input device 402 has toggled off. Conversely, in another exemplary implementation, only a threshold number of noise indicator signals 414-A (e.g., more than half, etc.) may need to be in agreement that the predetermined system noise threshold is not exceeded in order to make such a detection.

Signal output facility 416 may adjust weighting factors in any suitable way such as to cause audio input device 402 to be completely cut out of the mix, fully included in the mix, or anything in between (e.g., emphasizing or deemphasizing audio input captured by an audio input device 402 to any degree as may serve a particular implementation). Additionally, weighting factors may be adjusted in accordance with any suitable timeline, such as by being adjusted gradually so as to make an input fade in or fade out in a non-distracting and non-disorienting manner.

Figure 11:
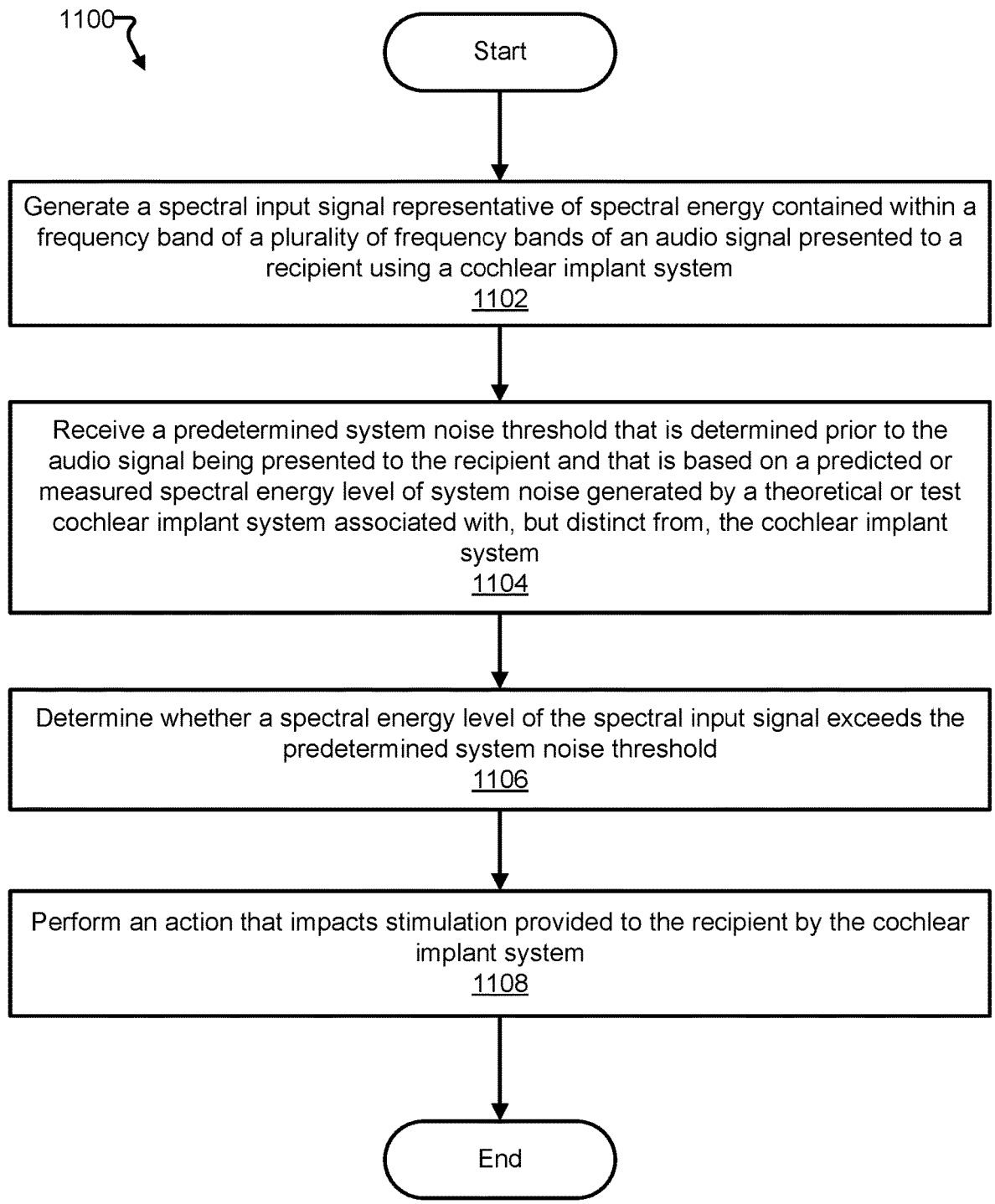
FIG. 11 illustrates an exemplary method of detecting and reacting to system noise generated by a cochlear implant system according to principles described herein.

FIG. 11 illustrates an exemplary method 1100 for detecting and reacting to system noise generated by a cochlear implant system. While FIG. 11 illustrates exemplary steps according to one embodiment, other embodiments may omit, add to, reorder, and/or modify any of the steps shown in FIG. 11. One or more of the steps shown in FIG. 11 may be performed by sound processor 300 or any other suitable system described herein.

In operation 1102, a sound processor included in a cochlear implant system generates a spectral input signal representative of spectral energy contained within a frequency band of an audio input signal presented to a cochlear implant recipient. Operation 1102 may be performed in any of the ways described herein.

In operation 1104, the sound processor included in the cochlear implant system receives a predetermined system noise threshold that is determined prior to the audio input signal being presented to the recipient and that is based on a predicted or measured spectral energy level of system noise generated by a theoretical or test cochlear implant system associated with, but distinct from, the cochlear implant system. Operation 1104 may be performed in any of the ways described herein.

In operation 1106, the sound processor included in the cochlear implant system determines whether a spectral energy level of the spectral input signal exceeds a predetermined system noise threshold. Operation 1106 may be performed in any of the ways described herein.

In operation 1108, the sound processor included in the cochlear implant system performs an action that impacts stimulation provided to the recipient by the cochlear implant system. Operation 1108 may be performed, based on the determining, in operation 1106, of whether the spectral energy level of the spectral input signal exceeds the predetermined system noise threshold. For example, operation 1008 may include generating a spectral output signal by including the spectral input signal in the spectral output signal if the spectral energy level exceeds the predetermined system noise threshold, and excluding the spectral input signal from the spectral output signal if the spectral energy level does not exceed the predetermined system noise threshold. As another example, operation 1008 may include detecting a toggling off or on of a particular audio input device and revising, based on the detection of the toggling, a dynamic weighting factor assigned to an audio input signal. Operation 1108 may be performed in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A sound processor included in a cochlear implant system used by a recipient, the sound processor comprising:
    at least one physical computing component configured to:
        generate a spectral input signal, the spectral input signal representative of spectral energy contained within a frequency band of a plurality of frequency bands of an audio input signal presented to the recipient,
        receive a predetermined system noise threshold that is determined prior to the audio input signal being presented to the recipient and that is based on a predicted or measured spectral energy level of system noise generated by a theoretical or test cochlear implant system associated with, but distinct from, the cochlear implant system,
        determine whether a spectral energy level of the spectral input signal exceeds the predetermined system noise threshold, and
        perform, based on the determining of whether the spectral energy level of the spectral input signal exceeds the predetermined system noise threshold, an action that impacts stimulation provided to the recipient by the cochlear implant system.

2. The sound processor of claim 1, wherein the performing of the action that impacts the stimulation provided to the recipient includes generating a spectral output signal based on the determination of whether the spectral energy level of the spectral input signal exceeds the predetermined system noise threshold.

3. The sound processor of claim 2, wherein:
    the determining whether the spectral energy level of the spectral input signal exceeds the predetermined system noise threshold comprises determining that the spectral energy level of the spectral input signal exceeds the predetermined system noise threshold; and
    the generating of the spectral output signal comprises including the spectral input signal in the spectral output signal based on the determining that the spectral energy level of the spectral input signal exceeds the predetermined system noise threshold.

4. The sound processor of claim 2, wherein:
    the determining whether the spectral energy level of the spectral input signal exceeds the predetermined system noise threshold comprises determining that the spectral energy level of the spectral input signal does not exceed the predetermined system noise threshold; and
    the generating of the spectral output signal comprises excluding the spectral input signal from the spectral output signal based on the determining that the spectral energy level of the spectral input signal does not exceed the predetermined system noise threshold.

5. The sound processor of claim 4, wherein the generating of the spectral output signal comprises including a spectral signal representative of comfort noise in the spectral output signal in place of the spectral input signal based on the determining that the spectral energy level of the spectral input signal does not exceed the predetermined system noise threshold.

6. The sound processor of claim 1, wherein:
    the at least one physical computing component is further configured to:
        receive a plurality of audio input signals, including the audio input signal, from a plurality of audio input devices included in the cochlear implant system, and
        assign a dynamic weighting factor to each audio input signal of the plurality of audio input signals, the dynamic weighing factors configured to define how the plurality of audio input signals is mixed in the stimulation provided to the recipient;
    the audio input signal is assigned a particular dynamic weighting factor and is provided by a particular audio input device of the plurality of audio input devices; and
    the performing of the action that impacts the stimulation provided to the recipient includes:
        detecting, based on the determination of whether the spectral energy level of the spectral input signal exceeds the predetermined system noise threshold, a toggling off or on of the particular audio input device, and revising, based on the detection of the toggling, the particular dynamic weighting factor assigned to the audio input signal.

7. The sound processor of claim 1, wherein:
the generating of the spectral input signal comprises dividing the audio input signal into a plurality of spectral input signals each corresponding to a different respective frequency band in the plurality of frequency bands;
the spectral input signal is included in the plurality of spectral input signals;
the dividing of the audio input signal into the plurality of spectral input signals comprises processing the audio input signal in accordance with a Fast Fourier Transform (FFT) algorithm; and
each spectral input signal in the plurality of spectral input signals corresponds to a particular frequency bin included in a plurality of frequency bins associated with the FFT algorithm.

8. The sound processor of claim 1, wherein:
the generating of the spectral input signal comprises dividing the audio input signal into a plurality of spectral input signals each corresponding to a different respective frequency band in the plurality of frequency bands;
the spectral input signal is included in the plurality of spectral input signals;
the dividing of the audio input signal into the plurality of spectral input signals comprises processing the audio input signal in accordance with a Fast Fourier Transform (FFT) algorithm;
each spectral input signal in the plurality of spectral input signals corresponds to a respective stimulation channel of the cochlear implant system and corresponds to a frequency-contiguous set of frequency bins included in a plurality of frequency bins associated with the FFT algorithm; and
the spectral energy level of the spectral input signal is an average spectral energy of the frequency-contiguous set of frequency bins corresponding to the spectral input signal.

9. The sound processor of claim 1, wherein:
the receiving of the predetermined system noise threshold comprises:
receiving a test frequency domain signal, the test frequency domain signal representative of the predicted or measured spectral energy level of the system noise within the frequency band associated with the spectral input signal,
determining an amplitude of the test frequency domain signal, and
setting, prior to the audio input signal being presented to the recipient, the predetermined system noise threshold to a value within a predetermined amount of the determined amplitude of the test frequency domain signal; and
the received test frequency domain signal is determined based on a signal that is representative of system noise within the frequency band associated with the spectral input signal and that is captured by a microphone included in the test cochlear implant system while the test cochlear implant system is located within an anechoic chamber.

10. The sound processor of claim 1, wherein:
the receiving of the predetermined system noise threshold comprises:
receiving a test frequency domain signal, the test frequency domain signal representative of the predicted or measured spectral energy level of the system noise within the frequency band associated with the spectral input signal,
determining an amplitude of the test frequency domain signal, and
setting, prior to the audio input signal being presented to the recipient, the predetermined system noise threshold to a value within a predetermined amount of the determined amplitude of the test frequency domain signal; and
the setting of the predetermined system noise threshold is performed based on at least one of:
a variance of an average amplitude of spectral energy contained within the test frequency domain signal,
a pulse rate of the cochlear implant system,
a sample rate of the test frequency domain signal, and
an FFT update rate of the test frequency domain signal.

11. The sound processor of claim 1, wherein:
the at least one physical computing component is further configured to determine, based on a temporal average of spectral energy contained within the frequency band, whether a spectral energy level of the spectral input signal exceeds the predetermined system noise threshold;
the temporal average of the spectral energy contained within the frequency band comprises an average of a first amount of spectral energy contained within the frequency band and a second amount of spectral energy contained within the frequency band;
the first amount of spectral energy comprises an average of a plurality of measured amounts of spectral energy contained within the frequency band;
the second amount of spectral energy comprises a measured amount of spectral energy contained within the frequency band; and
each measured amount of spectral energy in the plurality of measured amounts of spectral energy is measured at different times prior to a measuring of the second amount of spectral energy.

12. The sound processor of claim 1, wherein the receiving of the predetermined system noise threshold comprises accessing data representative of the predetermined system noise threshold from a lookup table.

13. The sound processor of claim 1, wherein:
the predetermined system noise threshold is included in a noise profile associated with a configuration of the cochlear implant system; and
the receiving of the predetermined system noise threshold comprises accessing data representative of the noise profile associated with the configuration of the cochlear implant system by
receiving input representative of a selection of the noise profile, and
accessing, based on the input representative of the selection of the noise profile, the data representative of the noise profile from a library of noise profiles, the library of noise profiles comprising a plurality of noise profiles each associated with a different respective configuration of the cochlear implant system.

14. The sound processor of claim 1, wherein the at least one physical computing component is further configured to direct a cochlear implant implanted within the recipient to apply electrical stimulation representative of the spectral output signal.

15. A sound processor included in a cochlear implant system used by a recipient, the sound processor comprising:
at least one physical computing component configured to:
divide an audio input signal presented to the recipient into a plurality of spectral input signals, each spectral input signal in the plurality of spectral input signals representative of spectral energy contained within a respective frequency band in a plurality of frequency bands included in the audio input signal, the plurality of spectral input signals including a particular spectral input signal,
receive a predetermined system noise threshold that is determined prior to the audio input signal being presented to the recipient and that is based on a predicted or measured spectral energy level of system noise generated by a theoretical or test cochlear implant system associated with, but distinct from, the cochlear implant system,
determine whether a spectral energy level of the particular spectral input signal exceeds the predetermined system noise threshold, and
perform, based on the determining of whether the spectral energy level of the particular spectral input signal exceeds the predetermined system noise threshold, an action that impacts stimulation provided to the recipient by the cochlear implant system, and
direct a cochlear implant implanted within the recipient to apply the stimulation to the recipient.

16. The sound processor of claim 15, wherein the performing of the action that impacts the stimulation provided to the recipient includes generating a spectral output signal based on the determination of whether the spectral energy level of the particular spectral input signal exceeds the predetermined system noise threshold.

17. The sound processor of claim 16, wherein:
the determining whether the spectral energy level of the particular spectral input signal exceeds the predetermined system noise threshold comprises determining that the spectral energy level of the particular spectral input signal exceeds the predetermined system noise threshold; and
the generating of the spectral output signal comprises including the particular spectral input signal in the spectral output signal based on the determining that the spectral energy level of the particular spectral input signal exceeds the predetermined system noise threshold.

18. The sound processor of claim 16, wherein:
the determining whether the spectral energy level of the spectral input signal exceeds the predetermined system noise threshold comprises determining that the spectral energy level of the spectral input signal does not exceed the predetermined system noise threshold; and
the generating of the spectral output signal comprises excluding the spectral input signal from the spectral output signal based on the determining that the spectral energy level of the spectral input signal does not exceed the predetermined system noise threshold.

19. The sound processor of claim 15, wherein:
the at least one physical computing component is further configured to:
receive a plurality of audio input signals, including the audio input signal, from a plurality of audio input devices included in the cochlear implant system, and
assign a dynamic weighting factor to each audio input signal of the plurality of audio input signals, the dynamic weighing factors configured to define how the plurality of audio input signals is mixed in the stimulation provided to the recipient;
the audio input signal is assigned a particular dynamic weighting factor and is provided by a particular audio input device of the plurality of audio input devices; and
the performing of the action that impacts the stimulation provided to the recipient includes:
detecting, based on the determination of whether the spectral energy level of the spectral input signal exceeds the predetermined system noise threshold, a toggling off or on of the particular audio input device, and
revising, based on the detection of the toggling, the particular dynamic weighting factor assigned to the audio input signal.

20. The sound processor of claim 15, wherein the receiving of the predetermined system noise threshold comprises:
receiving a test frequency domain signal, the test frequency domain signal representative of the predicted or measured spectral energy level of the system noise within the frequency band associated with the particular spectral input signal, the system noise measured by way of a microphone included in the test cochlear implant system while the test cochlear implant system was located within an anechoic chamber;
determining an amplitude of the test frequency domain signal; and
setting, prior to the audio input signal being presented to the recipient, the predetermined system noise threshold to a value within a predetermined amount of the determined amplitude of the test frequency domain signal.

21. The sound processor of claim 15, wherein:
the dividing of the audio input signal into the plurality of spectral input signals comprises processing the audio input signal in accordance with a Fast Fourier Transform (FFT) algorithm;
each spectral input signal in the plurality of spectral input signals corresponds to a respective stimulation channel of the cochlear implant system and corresponds to a frequency-contiguous set of frequency bins in a plurality of frequency bins of the FFT algorithm;
the spectral energy level of the particular spectral input signal is an average spectral energy of the frequency-contiguous set of frequency bins corresponding to the particular spectral input signal.

22. A method comprising:
generating, by a sound processor included in a cochlear implant system associated with a recipient, a spectral input signal, the spectral input signal representative of spectral energy contained within a frequency band of a plurality of frequency bands of an audio input signal presented to the recipient;
receiving, by the sound processor, a predetermined system noise threshold that is determined prior to the audio input signal being presented to the recipient and that is based on a predicted or measured spectral energy level of system noise generated by a theoretical or test cochlear implant system associated with, but distinct from, the cochlear implant system;
determining, by the sound processor, whether a spectral energy level of the spectral input signal exceeds the predetermined system noise threshold; and
performing, by the sound processor and based on the determining of whether the spectral energy level of the spectral input signal exceeds the predetermined system noise threshold, an action that impacts stimulation provided to the recipient by the cochlear implant system.

23. The method of claim 22, wherein the performing of the action that impacts the stimulation provided to the recipient includes generating a spectral output signal based on the determining of whether the spectral energy level of the spectral input signal exceeds the predetermined system noise threshold.

24. The method of claim 23, wherein:
the determining whether the spectral energy level of the particular spectral input signal exceeds the predetermined system noise threshold comprises determining that the spectral energy level of the particular spectral input signal exceeds the predetermined system noise threshold;
the generating of the spectral output signal comprises including the spectral input signal in the spectral output signal based on the determining that the spectral energy level of the spectral input signal exceeds the predetermined system noise threshold;
the generating of the spectral input signal is performed by dividing the audio input signal into a plurality of spectral input signals each corresponding to a different respective frequency band in the plurality of frequency bands; and
the spectral input signal is included in the plurality of spectral input signals.

25. The method of claim 23, wherein:
the determining whether the spectral energy level of the spectral input signal exceeds the predetermined system noise threshold comprises determining that the spectral energy level of the spectral input signal does not exceed the predetermined system noise threshold; and
the generating of the spectral output signal comprises excluding the spectral input signal from the spectral output signal based on the determining that the spectral energy level of the spectral input signal does not exceed the predetermined system noise threshold.

26. The method of claim 22, further comprising:
receiving, by the sound processor from a plurality of audio input devices included in the cochlear implant system, a plurality of audio input signals including the audio input signal; and
assigning, by the sound processor, a dynamic weighting factor to each audio input signal of the plurality of audio input signals, the dynamic weighing factors configured to define how the plurality of audio input signals is mixed in the stimulation provided to the recipient;
wherein:
the audio input signal is assigned a particular dynamic weighting factor and is provided by a particular audio input device of the plurality of audio input devices; and
the performing of the action that impacts the stimulation provided to the recipient includes:
detecting, based on the determination of whether the spectral energy level of the spectral input signal exceeds the predetermined system noise threshold, a toggling off or on of the particular audio input device, and
revising, based on the detection of the toggling, the particular dynamic weighting factor assigned to the audio input signal.

* * * * *